(12) United States Patent
Runyon

(10) Patent No.: US 9,163,208 B2
(45) Date of Patent: *Oct. 20, 2015

(54) METHOD AND SYSTEM FOR BIOREACTION

(76) Inventor: Larry Runyon, Las Cruces, NM (US)

( * ) Notice: Subject to any disclaimer, the term of this patent is extended or adjusted under 35 U.S.C. 154(b) by 822 days.

This patent is subject to a terminal disclaimer.

(21) Appl. No.: 12/660,353

(22) Filed: Feb. 25, 2010

(65) Prior Publication Data

US 2010/0316446 A1 Dec. 16, 2010

Related U.S. Application Data

(63) Continuation-in-part of application No. 11/326,185, filed on Jan. 4, 2006, now Pat. No. 7,682,823.

(60) Provisional application No. 60/641,523, filed on Jan. 4, 2005.

(51) Int. Cl.
| | |
|---|---|
| *C12M 1/22* | (2006.01) |
| *C12M 3/00* | (2006.01) |
| *C12M 1/36* | (2006.01) |
| *C12M 1/00* | (2006.01) |

(52) U.S. Cl.
CPC ............... *C12M 41/48* (2013.01); *C12M 23/14* (2013.01); *C12M 23/44* (2013.01); *C12M 23/48* (2013.01); *C12M 23/58* (2013.01); *C12M 41/14* (2013.01)

(58) Field of Classification Search
CPC ...... C12M 23/14; C12M 23/44; C12M 23/58; C12M 23/48; C05F 17/0018; C12C 11/006

USPC ......... 435/304.1, 305.2, 305.3; 422/132, 141, 422/143, 145; 428/402.21; 71/64.11

See application file for complete search history.

(56) References Cited

U.S. PATENT DOCUMENTS

| | | | | |
|---|---|---|---|---|
| 5,227,068 | A * | 7/1993 | Runyon | 210/610 |
| 5,323,906 | A * | 6/1994 | Gouge et al. | 206/524.7 |
| 5,362,642 | A * | 11/1994 | Kern | 435/404 |
| 7,682,823 | B1 * | 3/2010 | Runyon | 435/305.2 |
| 2002/0110905 | A1 * | 8/2002 | Barbera-Guillem et al. | 435/294.1 |
| 2007/0269888 | A1 * | 11/2007 | Houtzager et al. | 435/373 |

* cited by examiner

*Primary Examiner* — Michael Hobbs
(74) *Attorney, Agent, or Firm* — Kermit D. Lopez; Luis M. Ortiz; Ortiz & Lopez, PLLC

(57) ABSTRACT

Novel bioreactor systems, adapted to provide continuous batch incubation of microbes, especially bacteria, are provided. Bioreactor bags are preloaded with inert microbes prior to being shipped to the user. The inert microbes may be substantially dry or in other inert forms, and are stored in soluble containers within the bioreactor bags. Multiple sterile, preloaded, disposable bioreactor bags are used in a self-contained housing. The bags are automatically incubated in the housing and dispensed, preferably into an irrigation system. The system provides serial batch production of useful microbes for a week or more, without further supervision or intervention. Methods of manufacture, methods of use, methods of sales, and methods of farming are also provided.

18 Claims, 15 Drawing Sheets

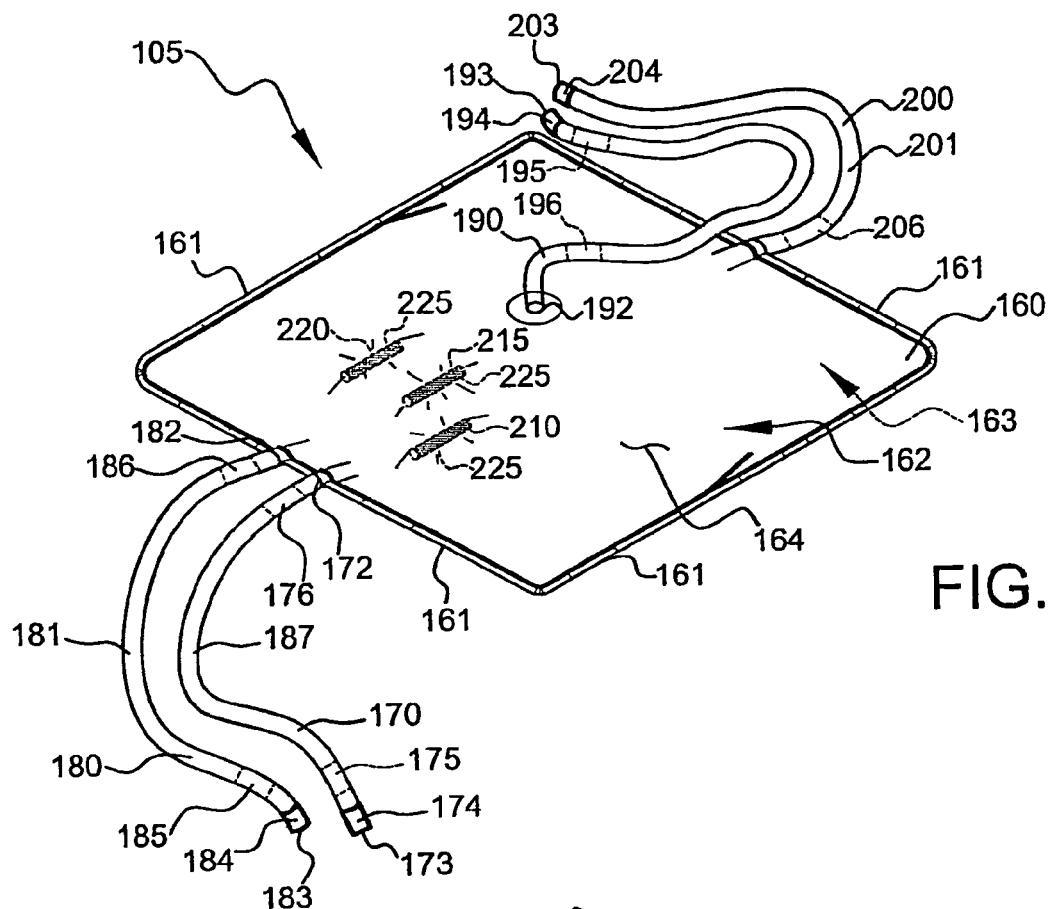
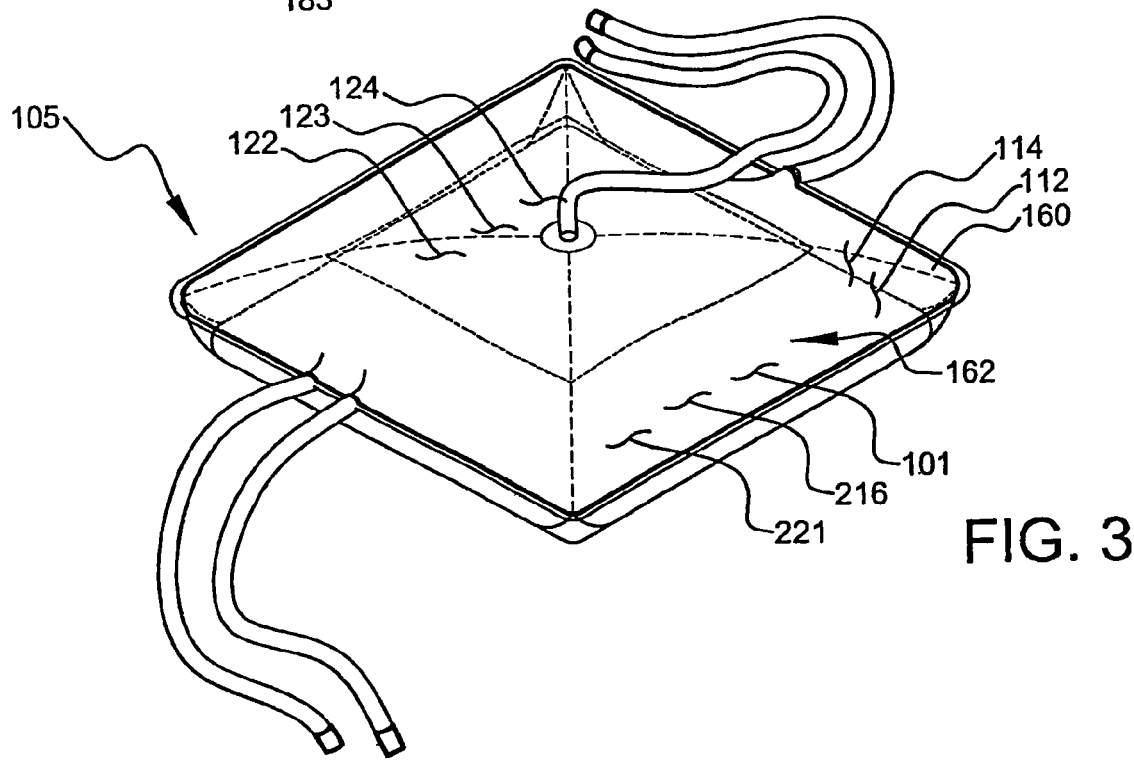

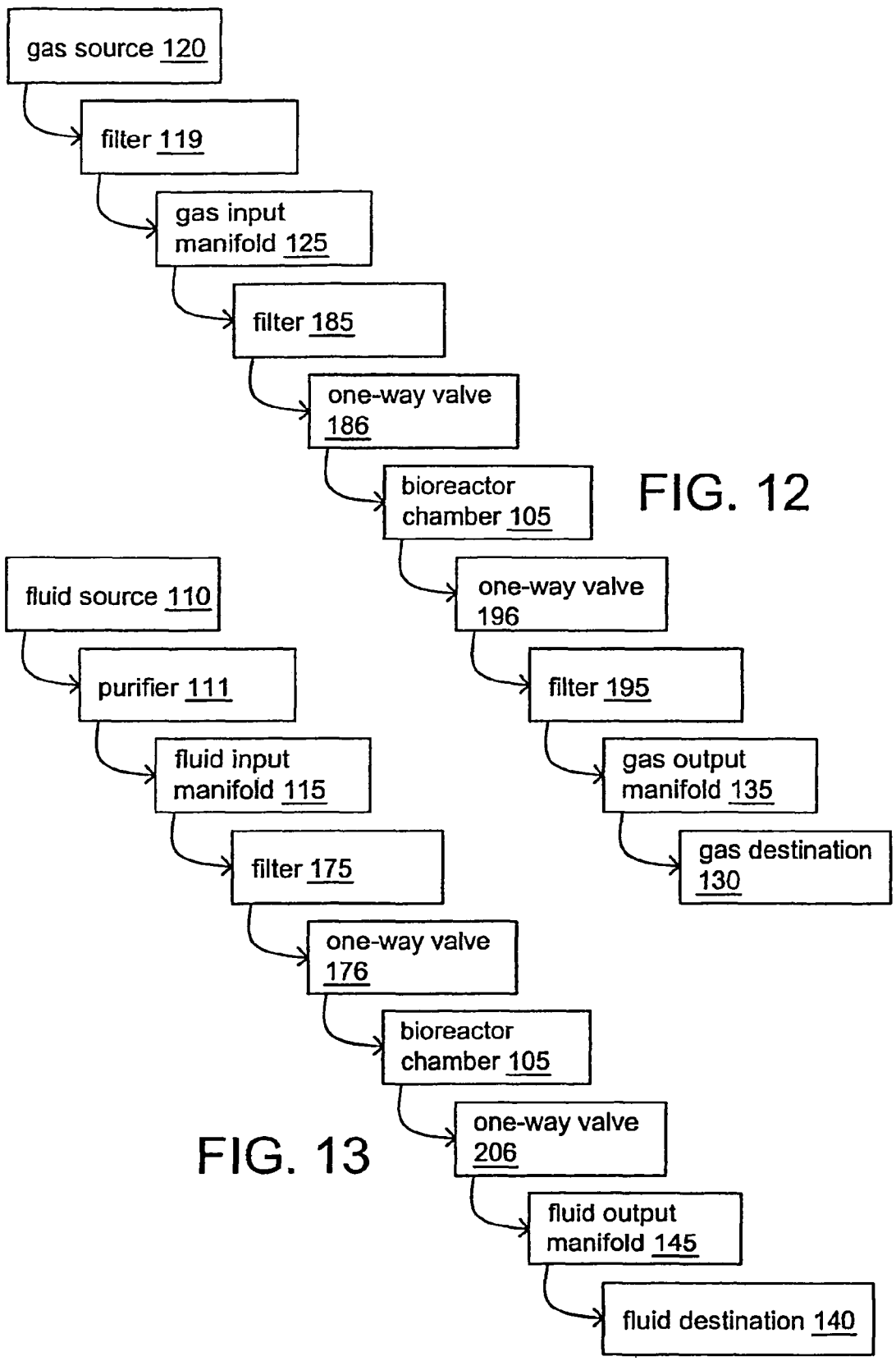

METHOD AND SYSTEM FOR BIOREACTION

RELATED APPLICATIONS

This application is a continuation-in-part of U.S. application Ser. No. 11/326,185, now U.S. Pat. No. 7,682,823, entitled BIOREACTOR SYSTEMS, filed on Jan. 4, 2006, which is related to and claims priority of U.S. Provisional application Ser. No. 60/641,523 entitled BIOREACTOR SYSTEMS, filed Jan. 4, 2005, the contents of each of which are incorporated herein by reference as if set forth in their entireties.

FIELD OF THE INVENTION

This invention relates to providing improved bioreactor systems and bioreaction methods. More particularly, this invention relates to providing improved bioreactors providing automatic serial batch production of live microbes. More particularly, this invention relates to providing improved bioreactors which use preloaded disposable bioreactor chambers.

BACKGROUND

Typically, bioreactors use a metal chamber to incubate one batch of microbes, and then such chamber must be sterilized between, each use. Disposable bioreactor chambers, such as bioreactor bags, must be manually monitored during use. Both these types of bioreactors are presently loaded with a starter culture of microbes at the beginning of the incubation process by the end-user, which increases the possibility of contamination of the bioreactor by pathogens, especially in agricultural settings.

Therefore, a need exists for a bioreactor system adapted to provide more-continuous batch incubation of microbes which system would provide for greatly decreased chances of such contamination.

OBJECTS AND FEATURES OF THE INVENTION

A primary object and feature of the present invention is to provide bioreactor systems. A further primary object and feature of the present invention is to provide bioreactor systems adapted to provide continuous batch incubation of microbes.

It is a further object and feature of the present invention to provide such a system having sterile preloaded bioreactor chambers. It is a further object and feature of the present invention to provide such a system comprising a self-contained housing for the sterile preloaded bioreactor chambers. It is a further object and feature of the present invention to provide such a system capable of running automatically for several days or weeks at a time.

It is a further object and feature of the present invention to provide methods of automating microbial treatment of specified biota growing in specified ground.

It is a further object and feature of the present invention to provide such a system comprising methods of manufacture, methods of use, methods of sales, and methods of farming.

A further primary object and feature of the present invention is to provide such a system that is efficient, inexpensive, and handy. Other objects and features of this invention will become apparent with reference to the following descriptions.

SUMMARY OF THE INVENTION

In accordance with an embodiment hereof, one aspect of this invention provides a bioreactor system, comprising: at least one bioreactor container adapted to contain at least one bioreaction; at least one microbe adapted to provide at least one living microbe; wherein such at least one microbe is in an inert state; and wherein such at least one microbe is stored within such at least one bioreactor container. The inert microbe may initially be in a substantially wet state or it may be in a substantially dry state.

Moreover, it provides such a bioreactor system, further comprising at least one first water-soluble container adapted to contain such at least one microbe in at least one water-soluble container. Additionally, it provides such a bioreactor system, further comprising at least one nutrient adapted to provide at least one nutrient adapted to support the life of such at least one at least one microbe, wherein such at least one at least one nutrient is in an inert, dry state; and wherein such at least one nutrient is stored within such at least one bioreactor container. Also, it provides such a bioreactor system, further comprising at least one second water-soluble container adapted to contain such at least one nutrient in at least one water-soluble container. In addition, it provides such a bioreactor system, further comprising at least one enzyme adapted to provide at least one enzyme adapted to support the life of such at least one at least one microbe, wherein such at least one at least one enzyme is in an inert, dry state; and wherein such at least one enzyme is stored within such at least one bioreactor container.

And, it provides such a bioreactor system, further comprising at least one third water-soluble container adapted to contain such at least one enzyme in at least one water-soluble container. Further, it provides such a bioreactor system, further comprising: at least one nutrient adapted to provide at least one nutrient adapted to support the life of such at least one at least one microbe, wherein such at least one at least one nutrient is in an inert, dry state; and wherein such at least one nutrient is stored within such at least one bioreactor container; at least one enzyme adapted to provide at least one enzyme adapted to support the life of such at least one at least one microbe, wherein such at least one at least one enzyme is in an inert, dry state; and wherein such at least one enzyme is stored within such at least one bioreactor container.

Even further, it provides such a bioreactor system, further comprising at least one fourth water-soluble container adapted to contain such at least one microbe, such at least one nutrient, and such at least one enzyme in at least one water-soluble container. Moreover, it provides such a bioreactor system, wherein such at least one microbe comprises at least one bacteria. Additionally, it provides such a bioreactor system, wherein such at least one bioreactor container comprises at least one flexible container. Also, it provides such a bioreactor system, wherein at least one interior of such at least one bioreactor container, containing such at least one microbe, is sterile of pathogens.

In accordance with another embodiment hereof, this invention provides a bioreactor system, comprising: at least one flexible container adapted to flexibly contain at least one fluid containing at least one cell culture; at least one fluid input adapted to input fluid into such at least one flexible container; at least one fluid output adapted to output fluid from such at least one flexible container; at least one gas input adapted to input at least one gas into such at least one flexible container; wherein such at least one gas input is adapted to create bubbles in such at least one fluid; at least one gas output adapted to output at least one gas from such at least one flexible container.

In addition, it provides such a bioreactor system, further comprising at least one fluid input manifold adapted to provide at least one fluid to such at least one fluid input. And, it provides such a bioreactor system, wherein such at least one fluid input manifold connects to a plurality of such at least one fluid inputs. Further, it provides such a bioreactor system, wherein such at least one fluid input comprises at least one connector adapted to connect to and disconnect from such at least one fluid input manifold without tools.

Even further, it provides such a bioreactor system, further comprising at least one fluid source adapted to provide at least one source of at least one fluid. Moreover, it provides such a bioreactor system, further comprising such at least one fluid, and wherein such at least one fluid comprises sterilized water. Additionally, it provides such a bioreactor system, wherein such sterilized water is sterilized with ultraviolet radiation treatment. Also, it provides such a bioreactor system, wherein such sterilized water is sterilized by reverse osmosis treatment. In addition, it provides such a bioreactor system, wherein such at least one fluid comprises temperature-controlled water.

And, it provides such a bioreactor system, further comprising at least one fluid output manifold adapted to receive fluid from such at least one fluid output. Further, it provides such a bioreactor system, wherein such at least one fluid output manifold connects to a plurality of such at least one fluid outputs. Even further, it provides such a bioreactor system, wherein such at least one fluid output comprises at least one connector adapted to quickly connect to and disconnect from such at least one fluid output manifold without tools. Moreover, it provides such a bioreactor system, further comprising at least one gas input manifold adapted to provide gas to such at least one gas input. Additionally, it provides such a bioreactor system, wherein such at least one gas input manifold connects to a plurality of such at least one gas inputs.

Also, it provides such a bioreactor system, wherein such at least one gas input comprises at least one connector adapted to quickly connect to and disconnect from such at least one gas input manifold without tools. In addition, it provides such a bioreactor system, further comprising at least one gas source adapted to provide at least one source of gas to such at least one gas input manifold. And, it provides such a bioreactor system, wherein such at least one gas source comprises at least one gas pump. Further, it provides such a bioreactor system, further comprising atmospheric air, wherein such atmospheric air comprises such at least one gas source. Even further, it provides such a bioreactor system, wherein such at least one gas source comprises at least one oxygen generator. Moreover, it provides such a bioreactor system, wherein such at least one gas source comprises at least one compressed gas container.

Additionally, it provides such a bioreactor system, further comprising at least one gas output manifold adapted to receive gas from such at least one gas output. Also, it provides such a bioreactor system, wherein such at least one gas output manifold connects to a plurality of such at least one gas outputs. In addition, it provides such a bioreactor system, wherein such at least one gas output comprises quick-at least one connector adapted to quickly connecting to and disconnecting from such at least one gas output manifold. And, it provides such a bioreactor system, wherein such at least one flexible container has a volume of about 30 gallons. Further, it provides such a bioreactor system, wherein such at least one flexible container is opaque.

Even further, it provides such a bioreactor system, further comprising at least one rigid stackable container adapted to provide at least one rigid stackable container adapted to hold such at least one flexible container. Moreover, it provides such a bioreactor system, wherein such at least one rigid stackable container comprises at least one rigid stackable box. Additionally, it provides such a bioreactor system, wherein such at least one rigid stackable box comprises cardboard but other rigid materials may be used in other exemplary embodiments.

Also, it provides such a bioreactor system, wherein such at least one fluid input, such at least one fluid output, such at least one gas input, and such at least one gas output are each heat-sealed to such at least one flexible container. In addition, it provides such a bioreactor system, wherein such at least one fluid input comprises at least one one-way valve. And, it provides such a bioreactor system, wherein such at least one fluid output comprises at least one one-way valve. Further, it provides such a bioreactor system, wherein such at least one gas input comprises at least one one-way valve. Even further, it provides such a bioreactor system, wherein such at least one gas output comprises at least one one-way valve.

Moreover, it provides such a bioreactor system, wherein such at least one fluid input comprises at least one filter. Additionally, it provides such a bioreactor system, wherein such at least one gas input comprises at least one filter. Also, it provides such a bioreactor system, wherein such at least one gas output comprises at least one filter. In addition, it provides such a bioreactor system, wherein such at least one gas input comprises at least one aerator.

And, it provides such a bioreactor system, further comprising at least one controller adapted to control the contents of such at least one flexible container. Further, it provides such a bioreactor system, wherein such at least one controller controls the flow of fluid from such at least one fluid source to such at least one fluid input manifold. Even further, it provides such a bioreactor system, wherein such at least one controller controls the flow of fluid from such at least one fluid input manifold to such at least one fluid input. Moreover, it provides such a bioreactor system, wherein such at least one controller controls the flow of fluid from such at least one fluid output to such at least one fluid output manifold. Additionally, it provides such a bioreactor system, wherein such at least one controller controls the flow of fluid from such at least one fluid output manifold to at least one fluid destination. In other words, the controller controls which flexible container of the at least one flexible container has fluid delivered thereto and therefrom thereby determining which flexible container is utilized. Also, it provides such a bioreactor system, wherein such at least one controller controls the flow of gas from such at least one gas source to such at least one gas input manifold.

In addition, it provides such a bioreactor system, wherein such at least one controller controls the flow of gas from such at least one gas input manifold to such at least one gas input. And, it provides such a bioreactor system, wherein such at least one controller controls the flow of gas from such at least one gas output to such at least one gas output manifold. Further, it provides such a bioreactor system, wherein such at least one controller controls the flow of gas from such at least one gas output manifold to at least one gas destination. Even further, it provides such a bioreactor system, wherein such at least one controller comprises at least one programmable irrigation timer.

Moreover, it provides such a bioreactor system, further comprising at least one enclosure adapted to enclose at least such at least one flexible container. Additionally, it provides such a bioreactor system, wherein such at least one enclosure maintains such at least one flexible container at least one selected temperature. Also, it provides such a bioreactor system, wherein such at least one enclosure comprises at least one heat pump. In addition, it provides such a bioreactor system, wherein such at least one enclosure comprises at least one thermostat. And, it provides such a bioreactor system, wherein such at least one enclosure is thermally insulated. Further, it provides such a bioreactor system, wherein such at least one enclosure comprises at least one fluid input manifold adapted to provide fluid to such at least one fluid input. Even further, it provides such a bioreactor system, wherein such at least one enclosure comprises at least one fluid output manifold adapted to receive fluid from such at least one fluid output.

Moreover, it provides such a bioreactor system, wherein such at least one enclosure comprises at least one gas input manifold adapted to provide gas to such at least one gas input. Additionally, it provides such a bioreactor system, further comprising at least one gas source adapted to provide at least one source of gas to such at least one gas input manifold. Also, it provides such a bioreactor system, wherein such at least one enclosure comprises at least one gas output manifold adapted to receive gas from such at least one gas output. In addition, it provides such a bioreactor system, wherein such at least one enclosure comprises at least one controller adapted to control the contents of such at least one flexible container.

And, it provides such a bioreactor system, wherein such at least one enclosure encloses about eight of such at least one flexible containers. Further, it provides such a bioreactor system, wherein such at least one enclosure comprises at least one transport adapted to transporting such at least one enclosure. Even further, it provides such a bioreactor system, wherein such at least one transport comprises at least one wheel. Moreover, it provides such a bioreactor system, wherein such at least one enclosure comprises at least one access door.

Additionally, it provides such a bioreactor system, further comprising at least one irrigation system adapted to irrigate at least one crop. Also, it provides such a bioreactor system, further comprising at least one irrigation system input adapted to input such fluid output from such at least one flexible container into such at least one irrigation system. In addition, it provides such a bioreactor system, wherein such at least one irrigation system input comprises at least one fluid pump. And, it provides such a bioreactor system, wherein such at least one irrigation system input comprises at least one venturi suction unit. Further, it provides such a bioreactor system, wherein such at least one irrigation system input comprises at least one storage tank. Even further, it provides such a bioreactor system, wherein about 400 acres of crops are treated per 30 gallon flexible container.

In accordance with another embodiment hereof, this invention provides a bioreactor system, relating to housing and maintaining at least one bioreaction in at least two bioreactor chambers, comprising: at least one enclosure adapted to enclose such at least two bioreactor chambers; wherein such at least one enclosure is thermally insulated; wherein such at least one enclosure comprises at least one temperature control adapted to control at least one temperature within such at least one enclosure; wherein such at least one enclosure comprises at least one fluid input manifold adapted to provide at least one fluid to each of such at least two bioreactor chambers; wherein such at least one enclosure comprises at least one fluid output manifold adapted to receive fluid from each of such at least two bioreactor chambers; wherein such at least one enclosure comprises at least one gas input manifold adapted to provide gas to each of such at least two bioreactor chambers; wherein such at least one enclosure comprises at least one gas output manifold adapted to receive gas from each of such at least two bioreactor chambers; wherein such at least one enclosure comprises at least one controller adapted to control such at least one temperature control, such at least one fluid input manifold, such at least one fluid output manifold, such at least one gas input manifold, and such at least one gas output manifold.

Moreover, it provides such a bioreactor system, wherein such at least one controller comprises at least one programmable controller. Additionally, it provides such a bioreactor system, wherein such at least one temperature control comprises at least one heat pump. Also, it provides such a bioreactor system, wherein such at least one temperature control comprises at least one thermostat. In addition, it provides such a bioreactor system, further comprising at least one gas source adapted to provide at least one gas to such at least one gas input manifold. And, it provides such a bioreactor system, further comprising at least one fluid source adapted to provide at least one fluid to such at least one fluid input manifold. Further, it provides such a bioreactor system, wherein such at least one enclosure encloses about eight of such at least two bioreactor chambers. Even further, it provides such a bioreactor system, wherein such at least one enclosure comprises at least one transport adapted to transporting such at least one enclosure. Moreover, it provides such a bioreactor system, wherein such at least one transport comprises at least one wheel. Additionally, it provides such a bioreactor system, wherein such at least one enclosure comprises at least one access door.

In accordance with another embodiment hereof, this invention provides a bioreactor system, comprising: at least one flexible container adapted to flexibly contain at least one aqueous solution containing at least one cell culture; at least one fluid input adapted to input at least one fluid into such at least one flexible container; at least one fluid output adapted to output such at least one aqueous solution from such at least one flexible container; at least one gas input adapted to input at least one gas into such at least one flexible container; at least one gas output adapted to output at least one gas from such at least one flexible container; at least one enclosure adapted to enclose such at least one flexible container; wherein such at least one enclosure is thermally insulated; at least one temperature control adapted to control at least one temperature within such at least one enclosure; at least one fluid input manifold adapted to provide at least one fluid to such at least one fluid input; at least one fluid output manifold adapted to receive fluid from such at least one fluid output; at least one gas input manifold adapted to provide gas to such at least one gas input; at least one gas output manifold adapted to receive gas from such at least one gas output; and at least one controller adapted to control such at least one temperature control, such at least one fluid input manifold, such at least one fluid output manifold, such at least one gas input manifold, and such at least one gas output manifold.

In accordance with another embodiment hereof, this invention provides a method for bioreaction in a bioreactor system, comprising the steps of: selecting at least one inert microbe; selecting at least one dry, inert nutrient adapted to support the life of such at least one inert microbe; placing such at least one inert microbe and such at least one dry, inert nutrient into at least one sterile bioreactor chamber; and storing such at least one sterile bioreactor chamber containing such at least one inert microbe and such at least one dry, inert nutrient.

Also, it provides such a method further comprising the step of shipping such at least one sterile bioreactor chamber containing at least one inert microbe and such at least one dry, inert nutrient to at least one user. In addition, it provides such a bioreactor system, further comprising the steps of: adding water to such at least one sterile bioreactor chamber containing such at least one inert microbe and such at least one dry, inert nutrient; and permitting at least one bioreaction to occur.

And, it provides such a bioreactor system, further comprising the step of placing such at least one dry, inert microbe into at least one water-soluble container prior to placing such at least one dry, inert microbe into such at least one sterile bioreactor chamber. Further, it provides such a bioreactor system, further comprising the step of placing such at least one dry, inert nutrient into at least one water-soluble container prior to placing such at least one dry, inert nutrient into such at least one sterile bioreactor chamber. Even further, it provides such a bioreactor system, further comprising the steps of: selecting at least one dry, inert enzyme adapted to support the life of such at least one dry, inert microbe; placing such at least one dry, inert enzyme into such at least one sterile bioreactor chamber. Moreover, it provides such a bioreactor system, further comprising the step of placing such at least one dry, inert enzyme into at least one water-soluble container prior to placing such at least one dry, inert enzyme into such at least one sterile bioreactor chamber.

In accordance with another preferred embodiment hereof, this invention provides a bioreactor system, comprising the steps of: selecting at least one dry, inert microbe; selecting at least one dry, inert nutrient adapted to support the life of such at least one dry, inert microbe; selecting at least one previously sterilized bioreactor chamber; receiving such at least one bioreactor chamber containing such at least one dry, inert microbe and such at least one dry, inert nutrient from at least one manufacturer; installing such at least one bioreactor chamber containing such at least one dry, inert microbe and such at least one dry, inert nutrient in at least one bioreactor; adding fluid to such at least one bioreactor chamber containing such at least one dry, inert microbe and such at least one dry, inert nutrient; waiting for at least one bioreaction in such at least one bioreactor chamber to generate a useful number of live, active microbes; and harvesting such useful number of live, active microbes.

Additionally, it provides such a bioreactor system, further comprising the step of adding oxygen to such at least one bioreactor chamber, after such step of adding fluid to such at least one bioreactor chamber. Also, it provides such a bioreactor system, wherein such step of harvesting such useful number of live, active microbe comprises the step of adding such useful number of live, active microbes into at least one irrigation system. In addition, it provides such a bioreactor system, further comprising the steps of: uninstalling such at least one bioreactor chamber; and disposing of such at least one bioreactor chamber; after such step of harvesting such useful number of live, active microbes.

In accordance with another preferred embodiment hereof, this invention provides a bioreactor system, comprising the steps of: analyzing at least one soil for at least one user; developing at least one bioremediation prescription for such at least one analyzed soil; loading at least one bioreactor chamber with dry, inert microbes according to such at least one bioremediation prescription; providing such at least one loaded bioreactor chamber to such at least one user. And, it provides such a bioreactor system, further comprising the step of maintaining at least one bioreactor on such at least one user's site. Further, it provides such a bioreactor system, further comprising the step of remotely monitoring such at least one bioreactor. Even further, it provides such a bioreactor system, further comprising the step of installing such at least one loaded bioreactor chamber in at least one bioreactor on such at least one user's site.

Moreover, it provides such a bioreactor system, further comprising the step of installing such at least one loaded bioreactor chamber in at least one bioreactor on such at least one user's site according to at least one maintenance schedule. Additionally, it provides such a bioreactor system, further comprising the step of applying the bioreaction products of such at least one preloaded bioreactor chamber to such at least one analyzed soil. Also, it provides such a bioreactor system, further comprising the step of re-analyzing such at least one analyzed soil to determine the effects of applying such bioreaction products.

In accordance with another embodiment hereof, this invention provides a bioreactor system, comprising the steps of: analyzing at least one soil for at least one user; analyzing at least one chemical treatment history of such at least one soil; developing at least one bioremediation prescription for such at least one analyzed soil; providing at least one on-site bioreactor wherein such at least one on-site bioreactor comprises at least one programmable controller; providing at least one loaded bioreactor chamber containing dry, inert microbes, according to such at least one bioremediation prescription, adapted to be used with such on-site bioreactor; programming such at least one on-site bioreactor to incubate such microbes in such at least one loaded bioreactor chamber; and programming such at least one on-site bioreactor to dispense such incubated microbes.

In addition, it provides such a bioreactor system, wherein such step of developing at least one bioremediation prescription for such at least one analyzed soil is adapted to increase the functionality of crops grown in such at least one analyzed soil. And, it provides such a bioreactor system, wherein such step of developing at least one bioremediation prescription for such at least one analyzed soil is adapted to modify the growth of at least one cover crop grown in such at least one analyzed soil, wherein the modification of the growth of such at least one cover crop has at least one beneficial effect on the growth of at least one cash crop grown in such at least one analyzed soil after such at least one cover crop.

Further, it provides such a bioreactor system, wherein such step of developing at least one bioremediation prescription for such at least one analyzed soil is adapted to benefit bodies of water adjacent such at least one analyzed soil. Even further, it provides such a bioreactor system, wherein such step of developing at least one bioremediation prescription for such at least one analyzed soil is adapted to decrease the concentration of toxins of crops grown in such at least one analyzed soil.

In accordance with another embodiment hereof, this invention provides a bioreactor system, comprising: bioreactor container means for containing at least one bioreaction; microbe means for providing at least one living microbe; wherein such microbe means is in an inert, dry state; and wherein such microbe means is stored within such bioreactor container means.

Moreover, it provides such a bioreactor system, further comprising first water-soluble container means for containing such microbe means in at least one water-soluble container. Additionally, it provides such a bioreactor system, further comprising nutrient means for providing at least one nutrient adapted to support the life of such at least one microbe means, wherein such at least one nutrient means is in an inert, dry state; and wherein such nutrient means is stored within such bioreactor container means. Also, it provides such a bioreactor system, further comprising second water-soluble container means for containing such nutrient means in at least one water-soluble container.

In addition, it provides such a bioreactor system, further comprising enzyme means for providing at least one enzyme adapted to support the life of such at least one microbe means, wherein such at least one enzyme means is in an inert, dry state; and wherein such enzyme means is stored within such bioreactor container means. And, it provides such a bioreactor system, further comprising third water-soluble container means for containing such enzyme means in at least one water-soluble container. Further, it provides such a bioreactor system, further comprising: nutrient means for providing at least one nutrient adapted to support the life of such at least one microbe means, wherein such at least one nutrient means is in an inert, dry state; and wherein such nutrient means is stored within such bioreactor container means; enzyme means for providing at least one enzyme adapted to support the life of such at least one microbe means, wherein such at least one enzyme means is in an inert, dry state; and wherein such enzyme means is stored within such bioreactor container means.

Even further, it provides such a bioreactor system, further comprising fourth water-soluble container means for containing such microbe means, such nutrient means, and such enzyme means in at least one water-soluble container. Moreover, it provides such a bioreactor system, wherein such microbe means comprises at least one bacteria. Additionally, it provides such a bioreactor system, wherein such bioreactor container means comprises at least one flexible container. Also, it provides such a bioreactor system, wherein at least one interior of such bioreactor container means, containing such microbe means, is sterile of pathogens.

In accordance with another preferred embodiment hereof, this invention provides a bioreactor system, comprising: flexible container means for flexibly containing at least one fluid containing at least one cell culture; fluid input means for inputting fluid into such flexible container means; fluid output means for outputting fluid from such flexible container means; gas input means for inputting at least one gas into such flexible container means; wherein such gas input means is adapted to create bubbles in such at least one aqueous solution; gas output means for outputting at least one gas from such flexible container means. In addition, it provides such a bioreactor system, further comprising fluid input manifold means for providing fluid to such fluid input means. And, it provides such a bioreactor system, wherein such fluid input manifold means connects to a plurality of such fluid input means.

Further, it provides such a bioreactor system, wherein such fluid input means comprises connector means for connecting to and disconnecting from such fluid input manifold means without tools. Even further, it provides such a bioreactor system, further comprising fluid source means for providing at least one source of at least one fluid to such fluid input manifold means. Moreover, it provides such a bioreactor system, further comprising such at least one fluid, and wherein such at least one fluid comprises sterilized water. Additionally, it provides such a bioreactor system, wherein such sterilized water is sterilized with ultraviolet radiation treatment. Also, it provides such a bioreactor system, wherein such sterilized water is sterilized by reverse osmosis treatment. In addition, it provides such a bioreactor system, wherein such fluid source means comprises temperature-controlled water. And, it provides such a bioreactor system, further comprising fluid output manifold means for receiving fluid from such fluid output means.

Further, it provides such a bioreactor system, wherein such fluid output manifold means connects to a plurality of such fluid output means. Even further, it provides such a bioreactor system, wherein such fluid output means comprises connector means for quickly connecting to and disconnecting from such fluid output manifold means without tools. Moreover, it provides such a bioreactor system, further comprising gas input manifold means for providing at least one gas to such gas input means. Additionally, it provides such a bioreactor system, wherein such gas input manifold means connects to a plurality of such gas input means. Also, it provides such a bioreactor system, wherein such gas input means comprises connector means for quickly connecting to and disconnecting from such gas input manifold means without tools. In addition, it provides such a bioreactor system, further comprising gas source means for providing at least one source of gas to such gas input manifold means.

And, it provides such a bioreactor system, wherein such gas source means comprises at least one gas pump. Further, it provides such a bioreactor system, further comprising atmospheric air, wherein such atmospheric air comprises such gas source means. Even further, it provides such a bioreactor system, wherein such gas source means comprises at least one oxygen generator. Moreover, it provides such a bioreactor system, wherein such gas source means comprises at least one compressed gas container. Additionally, it provides such a bioreactor system, further comprising gas output manifold means for receiving gas from such gas output means. Also, it provides such a bioreactor system, wherein such gas output manifold means connects to a plurality of such gas output means.

In addition, it provides such a bioreactor system, wherein such gas output means comprises quick-connector means for quickly connecting to and disconnecting from such gas output manifold means. And, it provides such a bioreactor system, wherein such flexible container means has a volume of about 30 gallons. Further, it provides such a bioreactor system, wherein such flexible container means is opaque. Even further, it provides such a bioreactor system, further comprising rigid stackable container means for providing at least one rigid stackable container adapted to hold such flexible container means. Moreover, it provides such a bioreactor system, wherein such rigid stackable container means comprises at least one rigid stackable box. Additionally, it provides such a bioreactor system, wherein such at least one rigid stackable box comprises cardboard.

Also, it provides such a bioreactor system, wherein such fluid input means, such fluid output means, such gas input means, and such gas output means are each heat-sealed to such flexible container means. In addition, it provides such a bioreactor system, wherein such fluid input means comprises at least one one-way valve. And, it provides such a bioreactor system, wherein such fluid output means comprises at least one one-way valve. Further, it provides such a bioreactor system, wherein such gas input means comprises at least one one-way valve. Even further, it provides such a bioreactor system, wherein such gas output means comprises at least one one-way valve. Moreover, it provides such a bioreactor system, wherein such fluid input means comprises at least one filter. Additionally, it provides such a bioreactor system, wherein such gas input means comprises at least one filter. Also, it provides such a bioreactor system, wherein such gas output means comprises at least one filter. In addition, it provides such a bioreactor system, wherein such gas input means comprises at least one aerator.

And, it provides such a bioreactor system, further comprising controller means for controlling the contents of such flexible container means. Further, it provides such a bioreactor system, wherein such controller means controls the flow of fluid from such fluid source means to such fluid input manifold means. Even further, it provides such a bioreactor system, wherein such controller means controls the flow of fluid from such fluid input manifold means to such fluid input means. Moreover, it provides such a bioreactor system, wherein such controller means controls the flow of fluid from such fluid output means to such fluid output manifold means. Additionally, it provides such a bioreactor system, wherein such controller means controls the flow of fluid from such fluid output manifold means to at least one fluid destination. Also, it provides such a bioreactor system, wherein such controller means controls the flow of gas from such gas source means to such gas input manifold means. In addition, it provides such a bioreactor system, wherein such controller means controls the flow of gas from such gas input manifold means to such gas input means. And, it provides such a bioreactor system, wherein such controller means controls the flow of gas from such gas output means to such gas output manifold means. Further, it provides such a bioreactor system, wherein such controller means controls the flow of gas from such gas output manifold means to at least one gas destination. Even further, it provides such a bioreactor system, wherein such controller means comprises at least one programmable irrigation timer.

Even further, it provides such a bioreactor system, further comprising enclosure means for enclosing at least such flexible container means. Even further, it provides such a bioreactor system, wherein such enclosure means maintains such flexible container means at a selected temperature. Even further, it provides such a bioreactor system, wherein such enclosure means comprises at least one heat pump. Even further, it provides such a bioreactor system, wherein such enclosure means comprises at least one thermostat. Even further, it provides such a bioreactor system, wherein such enclosure means is thermally insulated. Even further, it provides such a bioreactor system, wherein such enclosure means comprises fluid input manifold means for providing fluid to such fluid input means. Even further, it provides such a bioreactor system, wherein such enclosure means comprises fluid output manifold means for receiving fluid from such fluid output means.

Even further, it provides such a bioreactor system, wherein such controller means comprises at least one programmable controller. Even further, it provides such a bioreactor system, wherein such temperature control means comprises at least one heat pump. Even further, it provides such a bioreactor system, wherein such temperature control means comprises at least one thermostat. Even further, it provides such a bioreactor system, further comprising gas source means for providing at least one gas to such gas input manifold means. Even further, it provides such a bioreactor system, further comprising fluid source means for providing at least one fluid to such fluid input manifold means. Even further, it provides such a bioreactor system, wherein such enclosure means encloses about eight of such at least two bioreactor chambers and a controller directs fluid to at least one of the eight bioreactor chambers to be utilized. Even further, it provides such a bioreactor system, wherein such enclosure means comprises transport means for transporting such enclosure means. Even further, it provides such a bioreactor system, wherein such transport means comprises at least one wheel. Even further, it provides such a bioreactor system, wherein such enclosure means comprises at least one access door.

Even further, it provides such a bioreactor system, further comprising irrigation system means for irrigating at least one crop. Even further, it provides such a bioreactor system, further comprising irrigation system input means for inputting such fluid output from such flexible container means into such irrigation system means. Even further, it provides such a bioreactor system, wherein such irrigation system input means comprises at least one fluid pump. Even further, it provides such a bioreactor system, wherein such irrigation system input means comprises at least one venturi suction unit. Even further, it provides such a bioreactor system, wherein such irrigation system input means comprises at least one storage tank. Even further, it provides such a bioreactor system, wherein about 400 acres of crops are treated per 30 gallon flexible container.

In accordance with another preferred embodiment hereof, this invention provides a bioreactor system, relating to housing and maintaining at least one bioreaction in at least two bioreactor chambers, comprising: enclosure means for enclosing such at least two bioreactor chambers; wherein such enclosure means is thermally insulated; wherein such enclosure means comprises temperature control means for controlling at least one temperature within such enclosure means; wherein such enclosure means comprises fluid input manifold means for providing at least one fluid to each of such at least two bioreactor chambers; wherein such enclosure means comprises fluid output manifold means for receiving fluid from each of such at least two bioreactor chambers; wherein such enclosure means comprises gas input manifold means for providing gas to each of such at least two bioreactor chambers; wherein such enclosure means comprises gas output manifold means for receiving gas from each of such at least two bioreactor chambers; wherein such enclosure means comprises controller means for controlling such temperature control means, such fluid input manifold means, such fluid output manifold means, such gas input manifold means, and such gas output manifold means.

Even further, it provides such a bioreactor system, wherein such controller means comprises at least one programmable controller. Even further, it provides such a bioreactor system, wherein such temperature control means comprises at least one heat pump. Even further, it provides such a bioreactor system, wherein such temperature control means comprises at least one thermostat. Even further, it provides such a bioreactor system, further comprising gas source means for providing at least one gas to such gas input manifold means. Even further, it provides such a bioreactor system, further comprising fluid source means for providing at least one fluid to such fluid input manifold means. Even further, it provides such a bioreactor system, wherein such enclosure means encloses about eight of such at least two bioreactor chambers. Even further, it provides such a bioreactor system, wherein such enclosure means comprises transport means for transporting such enclosure means. Even further, it provides such a bioreactor system, wherein such transport means comprises at least one wheel. Even further, it provides such a bioreactor system, wherein such enclosure means comprises at least one access door.

In accordance with another preferred embodiment hereof, this invention provides a bioreactor system, comprising: flexible container means for flexibly containing at least one aqueous solution containing at least one cell culture; fluid input means for inputting at least one fluid into such flexible container means; fluid output means for outputting such at least one aqueous solution from such flexible container means; gas input means for inputting at least one gas into such flexible container means; gas output means for outputting at least one gas from such flexible container means; enclosure means for enclosing such flexible container means; wherein such enclosure means is thermally insulated; temperature control means for controlling at least one temperature within such enclosure means; fluid input manifold means for providing at least one fluid to such fluid input means; fluid output manifold means for receiving fluid from such fluid output means; gas input manifold means for providing gas to such gas input means; gas output manifold means for receiving gas from such gas output means; and controller means for controlling such temperature control means, such fluid input manifold means, such fluid output manifold means, such gas input manifold means, and such gas output manifold means.

In accordance with another preferred embodiment hereof, this invention provides each and every novel feature, element, combination, step and/or method disclosed or suggested by this provisional patent application.

BRIEF DESCRIPTION OF THE DRAWING

The present invention is best understood from the following detailed description when read in conjunction with the accompanying drawing. It is emphasized that, according to common practice, the various features of the drawing are not necessarily to scale. On the contrary, the dimensions of the various features are arbitrarily expanded or reduced for clarity. Like numerals denote like features throughout the specification and drawing.

FIG. 2 shows a perspective view of a bioreactor chamber according to a preferred embodiment of the present invention.

FIG. 3 shows a perspective view of the bioreactor chamber of FIG. 2 with fluid added.

FIG. 12 shows a diagram of the path of gas through the bioreactor system.

FIG. 13 shows a diagram of the path of fluid through the bioreactor system.

DETAILED DESCRIPTION

Figure 1:
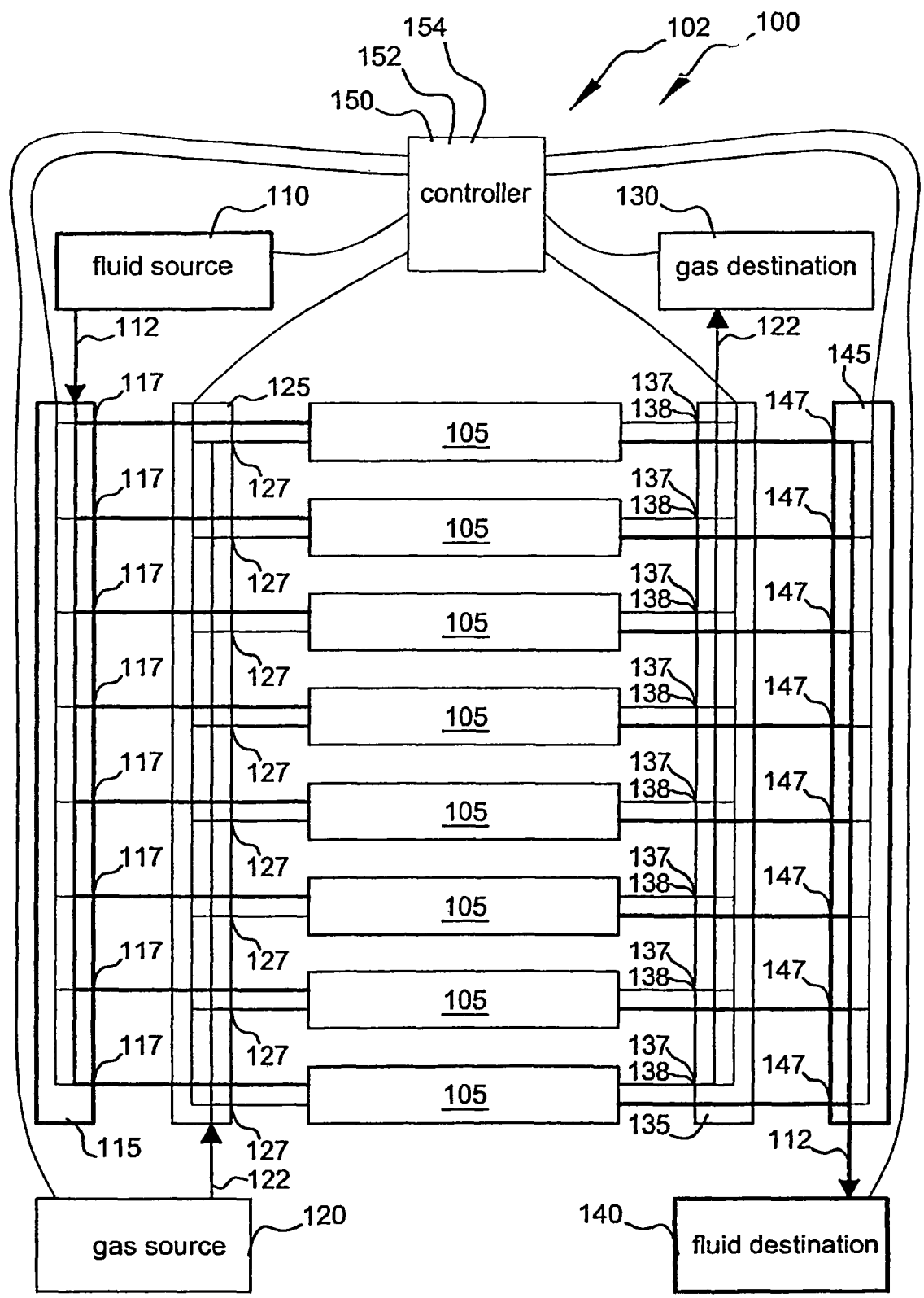
FIG. 1 shows a diagram of a bioreactor system according to a preferred embodiment of the present invention.

FIG. 1 shows a diagram of a bioreactor system 100 according to a preferred embodiment of the present invention; and FIG. 1 is further amplified and explained in reference to FIGS. 2-11 hereof. Preferably, bioreactor system 100 comprises bioreactor 102, as shown. Preferably, bioreactor 102 provides an apparatus for automatic serial batch production of desired live microbes 101. Preferably, bioreactor 102 comprises one or more bioreactor chambers 105, fluid source 110, fluid input manifold 115, gas source 120, gas input manifold 125, gas destination 130, gas output manifold 135, fluid destination 140, fluid output manifold 145, and at least one controller 150, as shown. Upon reading the teachings of this specification, those with ordinary skill in the art will now understand that, under appropriate circumstances, considering such issues as advances in technology, user preference, intended use, etc., other bioreactor components, such as sensors, sound generators, stirrers, starter culture injectors, light sources, fewer or more sources, inputs, outputs, manifolds or controllers, etc., may suffice.

For the purposes of this patent application, "microbes" are defined as organisms and/or cell cultures (capable of being grown in a bioreactor), such as, for example, bacteria, protazoa, yeasts, fungi, molds, algae, nematodes, mammalian cells, insect cells, other animal cells, plant cells, adherent cells on microcarriers, etc. Typically, for the agricultural purposes used as examples herein, "microbes" refers to aerobic bacteria.

Preferably, fluid source 110 comprises a source of fluid 112, suitable to supporting bioreactions, preferably sterilized water 114, as shown. Preferably, fluid source 110 provides sterile pH adjusted water adapted to support the maximum reproductive rate of particular microbes, such as, for example, a pH of between about 7 and about 6 for most aerobic bacteria, adjusted by means such as, for example, bubbling carbon dioxide through the water, as is known in the art of microbiology. Preferably, fluid source 110 provides temperature-controlled fluid 112, preferably at about 80 degrees Fahrenheit, so that fluid 112 entering bioreactor chambers 105 is the correct temperature for efficient microbial growth. Upon reading the teachings of this specification, those with ordinary skill in the art will now understand that, under appropriate circumstances, considering such issues as advances in technology, user preference, microbe species, desired growth rate, etc., other temperatures, such as 33 degrees Fahrenheit, 50 degrees Fahrenheit, 90 degrees Fahrenheit, etc., may suffice. Upon reading the teachings of this specification, those with ordinary skill in the art will now understand that, under appropriate circumstances, considering such issues as advances in technology, user preference, microbe requirements, etc., other fluids, such as mixtures of water and other chemicals, and such as glucose solution, liquid agar, seawater, etc., may suffice.

For the purposes of this patent application, a "bioreaction" means the growth and reproduction of live microbes 101 in bioreactor 102. For aerobic bacteria, water, oxygen, and nutrients are typically required for bioreaction; usually, a temperature of about 80 degrees Fahrenheit is preferred for efficient growth.

Preferably, fluid input manifold 115 distributes fluid 112 from fluid source 110 to each bioreactor chamber 105, as shown. Preferably, fluid input manifold 115 comprises one valve 117 for each bioreactor chamber 105, as shown. Preferably, each valve 117 is individually controlled by such at least one controller 150, so that fluid 112 may be individually supplied to each bioreactor chamber 105, as shown.

Figure 10:
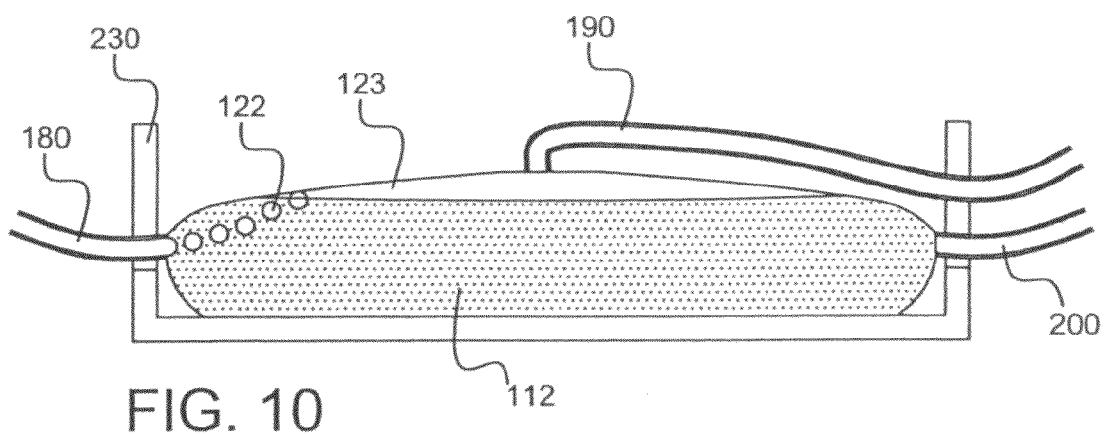
FIG. 10 shows a cross-sectional view of diagrammatic front view of the bioreactor chamber of FIG. 2 with fluid added, in use.
Figure 11:
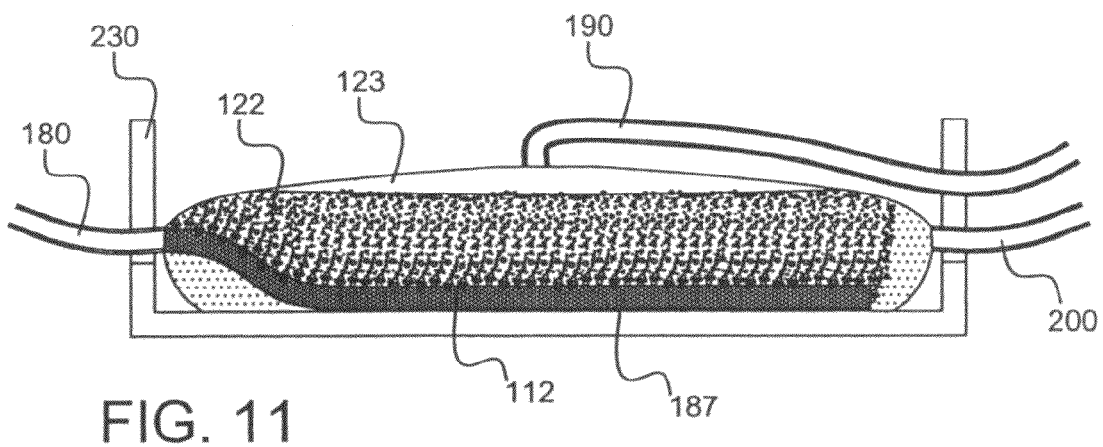
FIG. 11 shows a cross-sectional view of diagrammatic front view of the bioreactor chamber of FIG. 2 with fluid added, in use, with an aerator.

Preferably, gas source 120 comprises at least one source of gas 122 suitable to supporting bioreactions, as shown, such as, for example, oxygen. Preferably, gas 122 comprises atmospheric air 124. Preferably, gas source 120 provides gas 122 at sufficient pressure to bubble through fluid 112 in bioreactor chamber 105 (as shown in FIGS. 10 and 11). Preferably, gas source 122 is controlled by such at least one controller 150, as shown. Upon reading the teachings of this specification, those with ordinary skill in the art will now understand that, under appropriate circumstances, considering such issues as advances in technology, user preference, microbe species, etc., other gasses, such as synthetic oxygen/gas mixes, hydrogen sulfide, methane, etc., may suffice.

Preferably, gas input manifold 125 distributes gas 122 from gas source 120 to each bioreactor chamber 105, as shown. Preferably, gas input manifold 125 comprises one valve 127 for each bioreactor chamber 105, as shown. Preferably, each valve 127 is individually controlled by controller 150, so that gas 122 may be individually supplied to each bioreactor chamber 105, as shown.

Preferably, gas output manifold 135 receives gas 122 (typically enriched in carbon dioxide by the bioreaction) from each bioreactor chamber 105, as shown. Preferably, gas output manifold 135 comprises one valve 137 for each bioreactor chamber 105, as shown. Preferably, each valve 137 is individually controlled by the at least one controller 150, so that gas 122 may be individually released from each bioreactor chamber 105 (and/or held in each bioreactor chamber 105), as shown. Preferably, each valve 137 also serves as a gas relief valve 138, which automatically relieves serious excess gas 122 pressure in bioreactor chamber 105 while maintaining headspace 123, as shown. Upon reading the teachings of this specification, those with ordinary skill in the art will now understand that, under appropriate circumstances, considering such issues as advances in technology, user preference, intended use, etc., other arrangements, such as a separate gas relief valve attached to the bioreactor chamber, a single gas relief valve attached to the gas output manifold, a gas relief valve in each gas input tube, etc., may suffice.

Preferably, gas destination 130 receives gas 122 from gas output manifold 135, as shown. Preferably, gas destination 130 vents gas 122 to the atmosphere. Preferably, where suitable, gas destination 130 is controlled by the at least one controller 150, as shown. Upon reading the teachings of this specification, those with ordinary skill in the art will now understand that, under appropriate circumstances, considering such issues as advances in technology, user preference, type of gas, etc., other arrangements, such as venting into a container, venting into a greenhouse, etc., may suffice.

Preferably, fluid output manifold 145 receives fluid 112 (typically enriched in live microbes 101 by the bioreaction) from each bioreactor chamber 105, as shown. Preferably, fluid output manifold 145 comprises one valve 147 for each bioreactor chamber 105, as shown. Preferably, each valve 147 is individually controlled by the at least one controller 150, so that fluid 122 may be individually released from each bioreactor chamber 105 and/or held in each bioreactor chamber 105, i.e. the controller 150 may control the valves 147 such that fluid 122 may be held in one bioreactor chamber 105 while fluid 122 is released from another bioreactor chamber 105, as shown.

Preferably, fluid destination 140 receives fluid 112 from fluid output manifold 145, as shown. Preferably, fluid output manifold 145 is connected to pump 148, as shown in FIG. 7.

Figure 7:
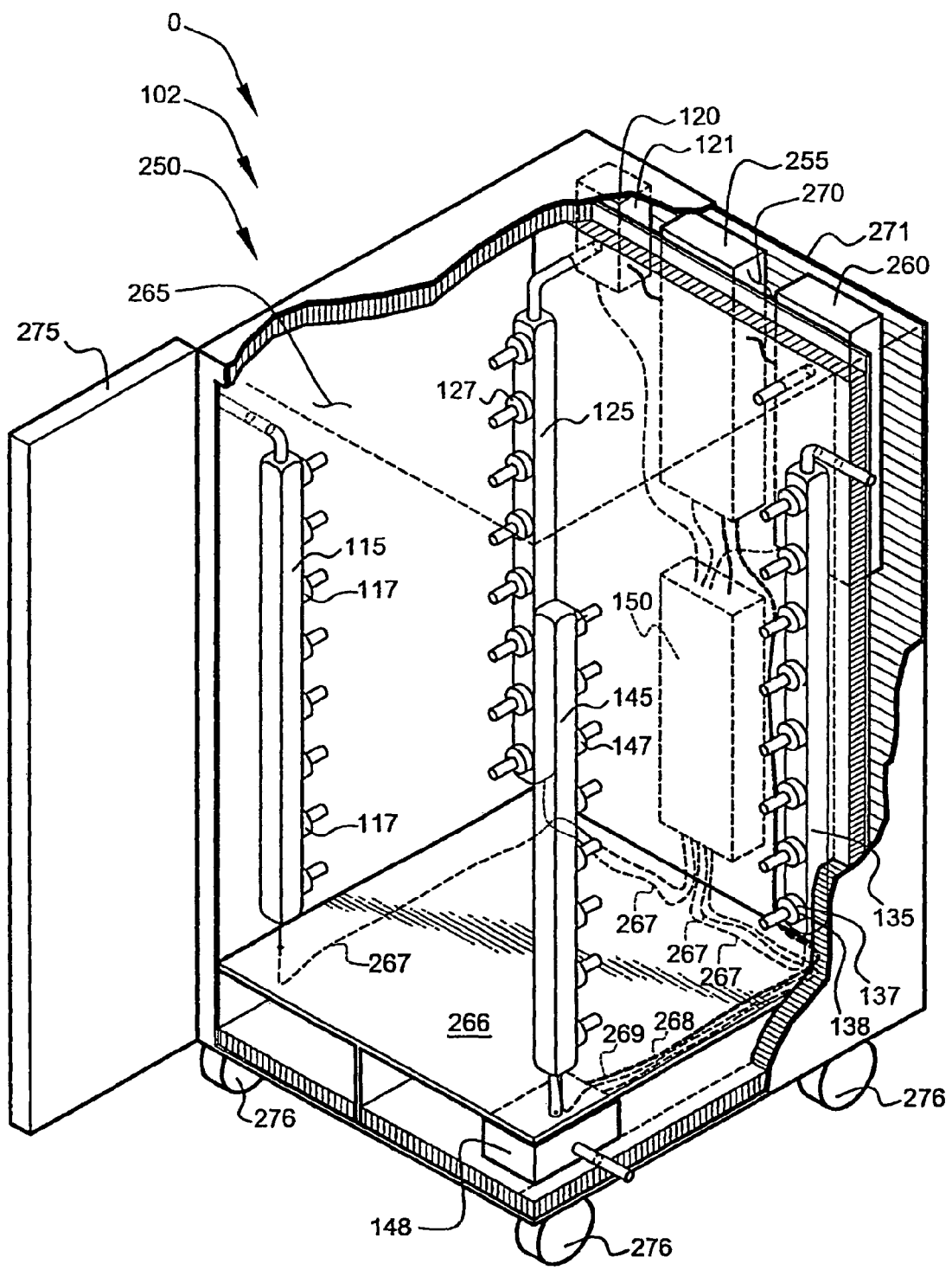
FIG. 7 shows a bioreactor housing according to a preferred embodiment of the present invention.
Figure 15:
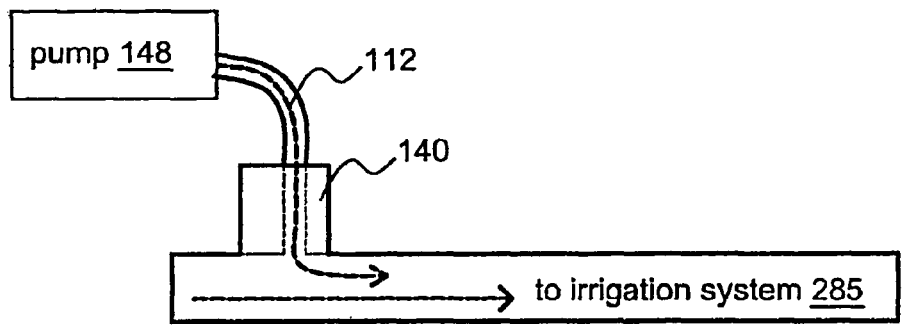
FIG. 15 shows a diagram of fluid output directly into an irrigation system.

Preferably, pump 148 is controlled by the at least one controller 150, as shown in FIG. 7, so that fluid 122 may be pumped from fluid output manifold 145 at a controlled rate. Preferably, fluid destination 140 delivers fluid 112 where it is needed to be used, such as, for example, directly into an irrigation system 285, as shown in FIG. 15.

Preferably, fluid input manifold 115, gas input manifold 125, gas output manifold 135, and fluid output manifold 145 are reusable and sterilizable. More preferably, fluid input manifold 115, gas input manifold 125, gas output manifold 135, and fluid output manifold 145 are reusable and autoclavable. Most preferably, fluid input manifold 115, gas input manifold 125, gas output manifold 135, and fluid output manifold 145 are stainless steel. Upon reading the teachings of this specification, those with ordinary skill in the art will now understand that, under appropriate circumstances, considering such issues as advances in technology, user preference, etc., other manifold materials, such as disposable plastic tubing, molded plastic, other metals, etc., may suffice.

Preferably, the at least one controller 150 comprises at least one programmable electronic controller 152, as shown, such as, for example, an irrigation timer 154, as shown. Preferably, the at least one controller 150 is programmable to add fluid 112 and gas 122 to one bioreactor chamber 105 after another (and to release fluid 112 and gas 122 from the bioreactor chamber 105), as shown, by opening and closing the valves (preferably solenoid-controlled valves) on the manifolds, on a timed schedule programmable by a user. Upon reading the teachings of this specification, those with ordinary skill in the art will now understand that, under appropriate circumstances, considering such issues as advances in technology, user preference, etc., other controllers, such as computers, multiple timers, a single controller controlling multiple bioreactors, etc., may suffice.

FIG. 2 shows a perspective view of a bioreactor chamber 105 according to a preferred embodiment of the present invention. Preferably, bioreactor chamber 105 comprises a sterile, disposable, flexible container, as shown. Preferably, bioreactor chamber 105 comprises bag 160, fluid input 170, gas input 180, gas output 190, and fluid output 200, as shown. Upon reading the teachings of this specification, those with ordinary skill in the art will now understand that, under appropriate circumstances, considering such issues as advances in technology, user preference, etc., other bioreactor chamber arrangements, such as other input and/or output ports, multiple compartments, rigid containers, other input and/or output port placements, etc., may suffice.

Preferably, bag 160 comprises at least one strong, flexible, plastic bag, preferably about three feet wide by about three feet long, with a useful volume of about 50 gallons, having a top surface 162 and a bottom surface 163, sealed on all four edges 161, as shown. Preferably, for culturing soil bacteria, bag 160 is opaque to protect live microbes 101 from accidental exposure to light during bioreaction. Preferably, the interior 164 of bag 160 is sterile prior to use. Upon reading the teachings of this specification, those with ordinary skill in the art will now understand that, under appropriate circumstances, considering such issues as advances in technology, user preference, intended use, etc., other bag sizes, such as one-half gallon, ten gallons, five hundred gallons, and other bag shapes, etc., may suffice.

For the purposes of this patent application, the term "sterile" means the absence of live (or dormant) pathogens, such as, for example, unwanted anaerobic bacteria. Bioreactors 105 may be sterilized by heat and/or radiation prior to inserting inert microbes 210. A bioreactor 105 containing only desired live microbes 101, or only desired inert microbes 210, has a "sterile" interior 164. For the purposes of this patent application, it should be understood that inert microbes 210 may be in various states such as substantially wet or substantially dry, even though the following exemplary embodiments often and generally refer to the embodiment in which the inert microbes are substantially dry, inert microbes.

Preferably, fluid input 170 comprises a flexible plastic tube 171, as shown, which is preferably heat-sealed into one edge 161 of bag 160 at the first end 172, as shown. Preferably, the second end 173 comprises a connector 174, adapted to sealably connect to a valve 117 on fluid input manifold 115 without the need for tools, as shown. Connectors of this type, commonly called "quick-release connectors", are well known in the art of laboratory gas and liquid manifolds. Preferably, fluid input 170 comprises a filter 175 to further purify fluid 122 going into bag 160, as shown. Preferably, fluid input 170 comprises one-way valve 176, which is preferably adapted to permit fluid 122 to flow from second end 173 to first end 172, while preventing fluid 122 from flowing in the other direction, as shown. Upon reading the teachings of this specification, those with ordinary skill in the art will now understand that, under appropriate circumstances, considering such issues as advances in technology, user preference, etc., other arrangements, such as no one-way valve, no filter, a quick connector between the fluid input and the bag, etc., may suffice.

Preferably, gas input 180 comprises a flexible plastic tube 181, as shown, which is preferably heat-sealed into one edge 161 of bag 160 at the first end 182, as shown. Preferably, the second end 183 comprises a connector 184, adapted to sealably connect to a valve 118 on gas input manifold 125, as shown, without the need for tools. Preferably, gas input 180 comprises a filter 185 to further purify gas 122 going into bag 160, as shown. Preferably, gas input 180 comprises one-way valve 186, which is preferably adapted to permit gas 122 to flow from second end 183 to first end 182, while preventing gas 122 from flowing in the other direction, as shown. Upon reading the teachings of this specification, those with ordinary skill in the art will now understand that, under appropriate circumstances, considering such issues as advances in technology, user preference, etc., other arrangements, such as no one-way valve, no filter, a quick connector between the gas input and the bag, etc., may suffice.

Preferably, gas output 190 comprises a flexible plastic tube 191, as shown, which is preferably heat-sealed into the top surface 162 of bag 160 at the first end 192, as shown. Preferably, the second end 193 comprises a connector 194, adapted to sealably connect to a valve 137 on gas output manifold 135, as shown, without the need for tools. Preferably, gas output 190 comprises a filter 195 to purify gas 122 leaving bag 160, as shown. Preferably, gas output 190 comprises one-way valve 196, which is preferably adapted to permit gas 122 to flow from first end 192 to second end 193, while preventing gas 122 from flowing in the other direction, as shown. Upon reading the teachings of this specification, those with ordinary skill in the art will now understand that, under appropriate circumstances, considering such issues as advances in technology, user preference, etc., other arrangements, such as no one-way valve, no filter, a quick connector between the gas output and the bag, etc., may suffice.

Preferably, fluid output 200 comprises a flexible plastic tube 201, as shown, which is preferably heat-sealed into one edge 161 of bag 160 at the first end 202, as shown. Preferably, the second end 203 comprises a connector 204, adapted to sealably connect to a valve 147 on fluid output manifold 145, as shown, without the need for tools. Preferably, fluid output 200 comprises one-way valve 206, which is preferably adapted to permit fluid 122 to flow from first end 202 to second end 203, while preventing fluid 122 from flowing in the other direction, as shown. Upon reading the teachings of this specification, those with ordinary skill in the art will now understand that, under appropriate circumstances, considering such issues as advances in technology, user preference, etc., other arrangements, such as no one-way valve, a filter, a quick connector between the fluid output and the bag, etc., may suffice.

Preferably, prior to use, bag 160 is sterilized and is then preloaded with at least one of inert microbes 210, dry, inert nutrient 215, and dry, inert enzymes 220, as shown. Preferably, dry, inert microbes 210, dry, inert nutrient 215, and dry, inert enzymes 220 are contained in water-soluble capsules 225, as shown. Preferably, water-soluble capsules 225 comprise polyvinyl alcohol plastic or other water-soluble plastics known in the art of packaging. Preferably, water-soluble capsules 225 are placed into bag 160 prior to adding fluid 112 to bag 160, as shown, preferably prior to bag 160 being stored prior to adding fluid 112, most preferably prior to bag 160 being shipped to the user prior to adding fluid 112. Upon reading the teachings of this specification, those with ordinary skill in the art will now understand that, under appropriate circumstances, considering such issues as advances in technology, user preference, etc., other water-soluble capsules, such as other water-soluble materials, other water-soluble container types, water-soluble capsules with a known dissolution time delay or rate, etc., may suffice.

Preferably, when fluid 112 is added to bag 160, water-soluble capsules 225 dissolve, releasing dry, inert microbes 210, dry, inert nutrient 215, and dry, inert enzymes 220 into fluid 112, as shown. At this point, dry, inert microbes 210, dry, inert nutrient 215, and dry, inert enzymes 220 rehydrate and become live microbes 101, available nutrient 216, and/or activated enzymes 221 (as shown in FIG. 3), which proceed to bioreact (i.e., the live microbes 101 grow and multiply), resulting in an increased number of live microbes 101. Preferably, a useful quantity of live microbes 101 is generated within eight to twelve hours of adding fluid 112 to bag 160, depending on the species of live microbes 101, the temperature of fluid 112, the type and quantity of nutrient 215, etc. In other exemplary embodiments, other shorter or longer times such as a twenty hour time period, may be used.

Preferably, the end-user maintains a bioreactor 102 on the end-user's own site to provide an on-demand source of live microbes 101. By providing disposable bioreactor chambers 105 to end-users in a sterile, preloaded condition, ready for immediate use, the end-user is relieved from having to maintain a highly sterile environment wherein to load bioreactor chambers 105 with beneficial microbe starter cultures. Also, the end-user is relieved from most of the difficulty of sterilizing the bioreactor between uses (to prevent the growth of pathogenic microbes) as the disposable bioreactor chambers 105 are simply replaced. These conveniences are particularly useful to agricultural end-users.

A large variety of microbes (particularly bacteria) have been identified in the art as providing useful bioremediation effects when applied live in sufficient concentrations to soil, plants, and waterways. Preferably, the inert microbes 210, dry, inert nutrient 215, and/or dry, inert enzymes 220 are selected and loaded into bioreactor chambers 105 to meet the bioremediation needs of the particular end-user, which needs will vary depending on such factors as, for example, soil type and condition, type of crops (or turf), types of local pathogens, time of year, etc. Upon reading the teachings of this specification, those with ordinary skill in the art will now understand that, under appropriate circumstances, considering such issues as advances in technology, user preference, etc., other bioreactor chamber contents, such as antibodies, trace nutrients, etc., may suffice.

FIG. 3 shows a perspective view of bioreactor chamber 105 of FIG. 2 with fluid 112 added. Preferably, gas 122 and fluid 112 are added to bioreactor chamber 105 to start the bioreaction, as shown. Preferably, additional gas 122 is added to bioreactor chamber 105 on a schedule determined by the user to meet the metabolic needs of live microbes 101, such as, for example, continuously, for fifteen minutes per hour, only on bioreaction start-up, etc. Typically, it is not necessary to add additional fluid 112.

Preferably, a headspace 123 of gas 122 is maintained adjacent top surface 162 of bag 160, as shown, to provide a gas exchange interface with fluid 112, so that oxygen from gas 122 may be absorbed by fluid 112, and carbon dioxide generated by the bioreaction in fluid 112 may be released into headspace 123 (in the case of aerobic microbes). Preferably, gas relief valve 138 maintains the pressure required for headspace 123, as shown, without permitting the pressure to build up to undesirable levels (such as where bag 160 may burst). Preferably, valve 137 on gas output manifold 135 is open for active and used bioreactor chambers 105 (and gas relief valve 138 is relied on to control gas output), and is closed for unused bioreactor chambers 105 (to prevent contamination of the unused bioreactor chambers 105).

Figure 4:
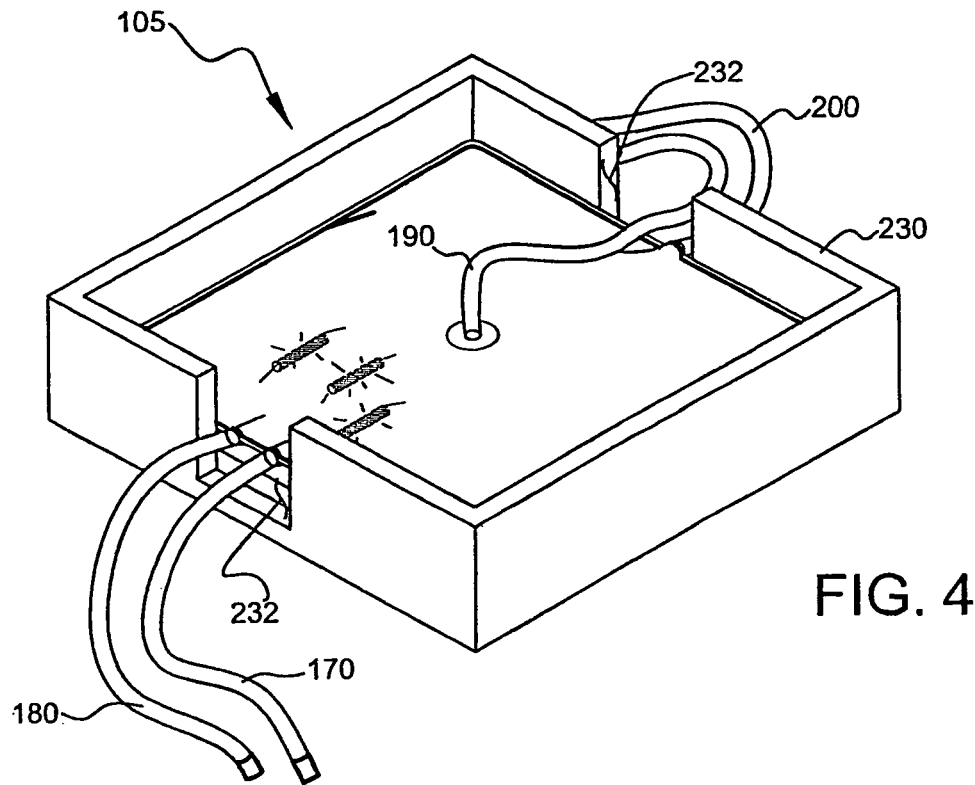
FIG. 4 shows a perspective view of the bioreactor chamber of FIG. 2 in a container.

FIG. 4 shows a perspective view of the bioreactor chamber 105 of FIG. 2 in a container 230. Preferably, bioreactor chambers 105 are held and supported during use in containers 230, as shown. Preferably, containers 230 are strong, stackable bins, about three feet wide by about three feet long by about nine inches deep, capable of supporting at least about three hundred and eighty pounds of fluid 122 (for 50-gallon bags 160, with about 45 gallons of fluid and about five gallons of headspace 123) in bioreactor chambers 105, as shown. Preferably, containers 230 comprise openings 232 adapted to permit the passage of fluid input 170, gas input 180, gas output 190, and fluid output 200, as shown. Preferably, containers 230 are reusable, such as, for example, sturdy plastic bins, as shown. In an alternate preferred embodiment, containers 230 are disposable, such as, for example, sturdy cardboard boxes.

Figure 5:
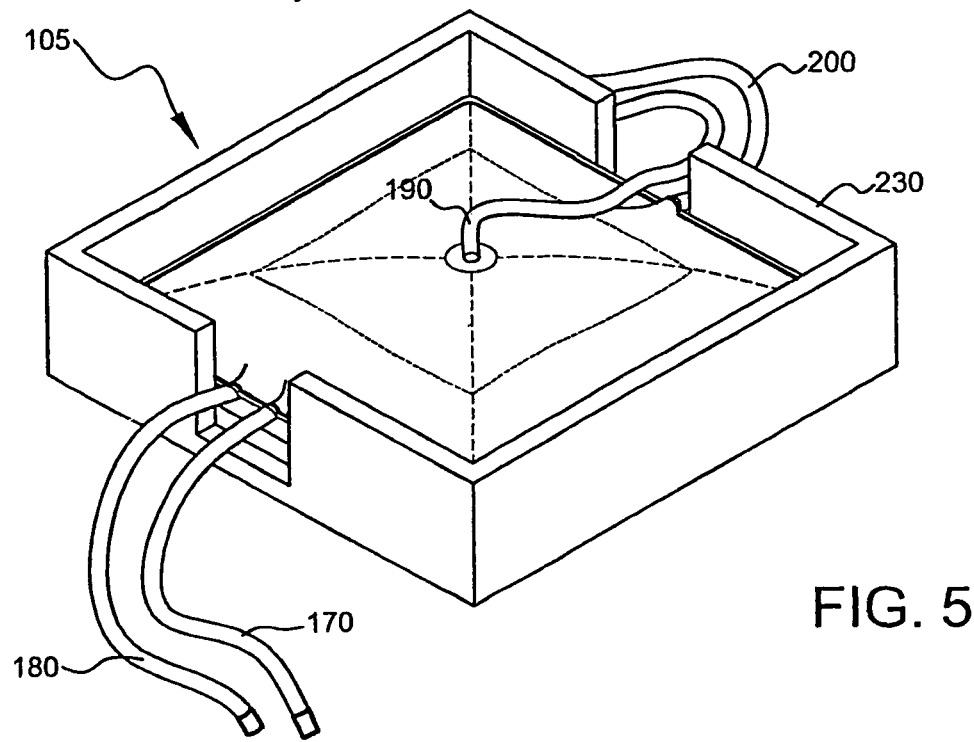
FIG. 5 shows a perspective view of the bioreactor chamber of FIG. 2 with fluid added, in a container.

FIG. 5 shows a perspective view of bioreactor chamber 105 of FIG. 2 with fluid 112 added, in a container 230. Preferably, containers 230 are tall enough to accommodate bioreactor chambers 105 in use, as shown.

Figure 6:
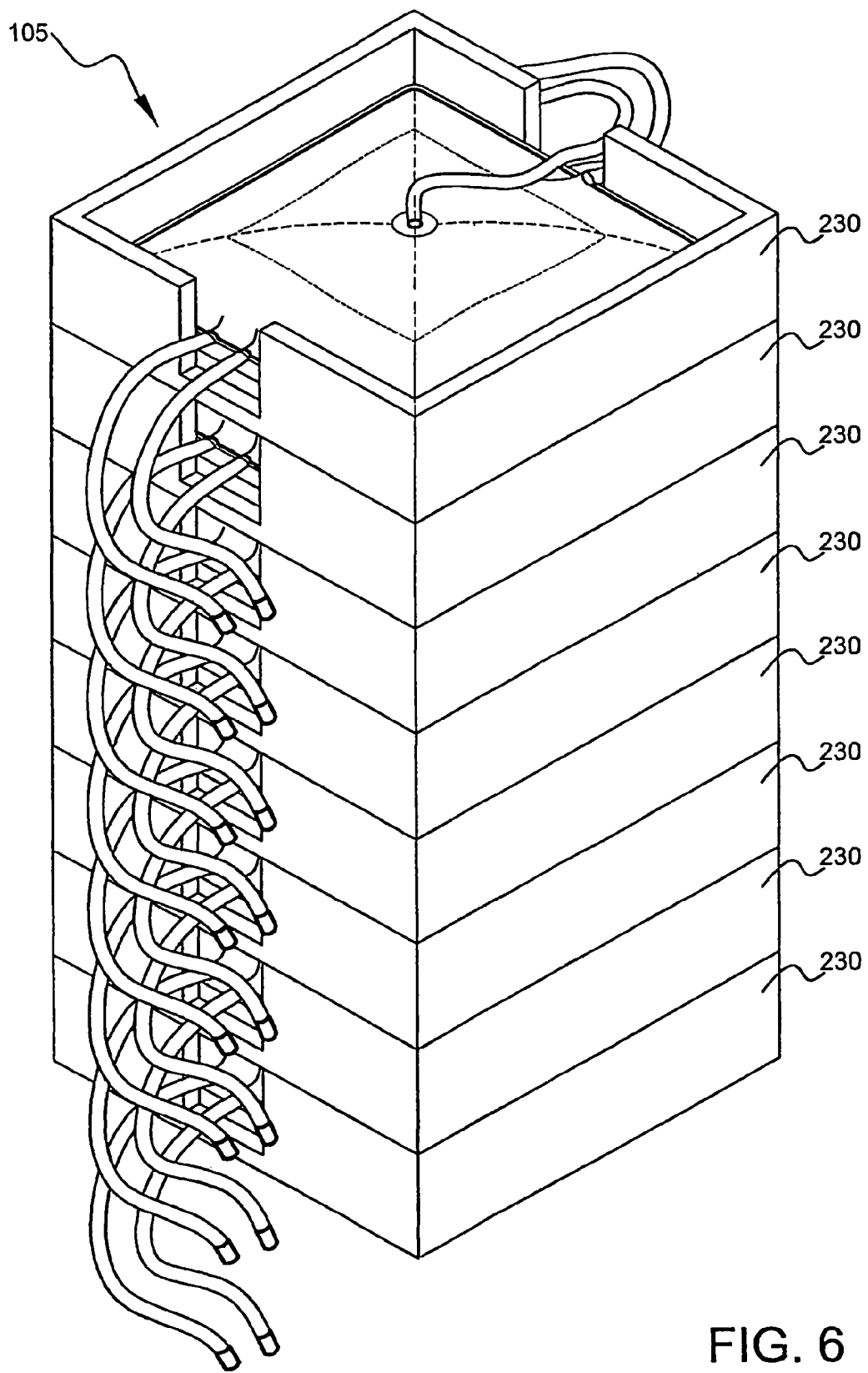
FIG. 6 shows a stack of bioreactor chambers in containers.

FIG. 6 shows a stack of bioreactor chambers 105 in containers 230. Preferably, multiple bioreactor chambers 105 in containers 230 are stacked to conserve space in bioreactor 102, as shown. Preferably, the multiple stacked bioreactor chambers 105 in containers 230 are hooked up to fluid input manifold 115, gas input manifold 125, gas output manifold 135, and fluid output manifold 145, as shown, and are automatically filled, incubated (i.e., bioreacted), and emptied one after the other according to the programming of controller 150. In an alternate preferred embodiment, depending on the strength of containers 230, multiple stacked bioreactor chambers 105 in containers 230 may be filled and incubated simultaneously.

FIG. 7 shows a bioreactor housing 250 according to a preferred embodiment of the present invention. Preferably, bioreactor 102 comprises housing 250, as shown. Preferably, housing 250 supports and contains at least fluid input manifold 115, gas input manifold 125, gas output manifold 135, fluid output manifold 145, and controller 150, as shown. Preferably, housing 250 also supports and contains pump 148, power source 255, and temperature regulator 260, as shown. Preferably, depending on the type of gas source 120, housing 250 also supports and contains gas source 120, as shown. Upon reading the teachings of this specification, those with ordinary skill in the art will now understand that, under appropriate circumstances, considering such issues as advances in technology, user preference, etc., other housing contents, such as sensors, lights, sound generators, other manifolds, etc., may suffice.

Preferably, housing 250 comprises enclosure 265, enclosure 270, and doors 275, as shown. Preferably, enclosure 265 comprises an insulated, lightproof enclosure, into which multiple stacked bioreactor chambers 105 in containers 230 may be placed, as shown. Preferably, enclosure 265 contains or provides access to fluid input manifold 115, gas input manifold 125, gas output manifold 135, and fluid output manifold 145, as shown.

Preferably, enclosure 265 comprises floor 266, as shown. Preferably, floor 266 is raised over the bottom of enclosure 265 to provide a space for the wiring 267 between controller 150 and each manifold, for pump 148, for the wiring 268 between pump 148 and controller 150, and for the wiring 269 between pump 148 and power source 255, as shown. Upon reading the teachings of this specification, those with ordinary skill in the art will now understand that, under appropriate circumstances, considering such issues as advances in technology, user preference, etc., other arrangements, such as no raised floor, other wiring, etc., may suffice.

Preferably, enclosure 270 comprises an air-vented enclosure, preferably on the back of housing 250, as shown. Preferably, enclosure 270 contains and supports controller 150, power source 255, and temperature regulator 260, as shown. Preferably, depending on the type of gas source 120, enclosure 270 also supports and contains gas source 120, as shown. Preferably, enclosure 270 comprises door 271, as shown, for maintenance access.

Preferably, power source 255 supplies electrical power to at least pump 148, controller 150, and temperature regulator 260, as shown. Preferably, depending on the type of gas source 120 (such as where gas source 120 is an air pump, as shown), power source 255 also supplies electrical power to gas source 120, as shown. Preferably, power source 255 plugs into a conventional power outlet. Upon reading the teachings of this specification, those with ordinary skill in the art will now understand that, under appropriate circumstances, considering such issues as advances in technology, user preference, etc., other power source arrangements, such as solar power, battery power, etc., may suffice.

Figure 22:
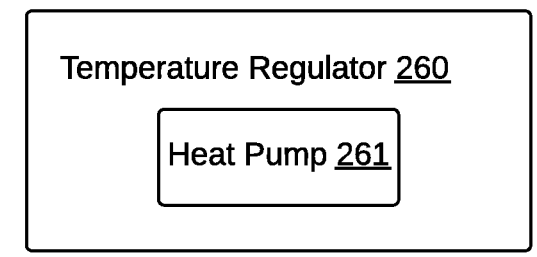
FIG. 22 illustrates a block diagram of the disclosed temperature regulator with a heat pump.

Preferably, temperature regulator 260 maintains a selected temperature in enclosure 265, such as, for example, a temperature of about eighty degrees Fahrenheit. Preferably, temperature regulator 260 comprises an electrical appliance capable of providing both heated and cooled air to enclosure 265, as shown, of the sort known in the art of heating and cooling appliances, such as, for example, a heat pump 261, as shown in FIG. 22. Preferably, temperature regulator 260 comprises thermostat 262, as shown, which senses the temperature in enclosure 265. Preferably, temperature regulator 260 is programmable. More preferably, temperature regulator 260 is controlled by controller 150, as shown, which is preferably programmable. Preferably, where live microbes 101 are stored and used over multiple days, temperature regulator 260 may decrease the temperature inside housing 250 to lower the metabolic rate of live microbes 101 between uses. Upon reading the teachings of this specification, those with ordinary skill in the art will now understand that, under appropriate circumstances, considering such issues as advances in technology, user preference, etc., other temperature regulators, such as, for example, a Peltier junction, separate heaters and coolers, individual temperature regulators for each bioreactor chamber, etc., may suffice.

Preferably, housing 250 comprises heavy-duty casters 276, so that housing 250 may be easily moved.

Figure 8:
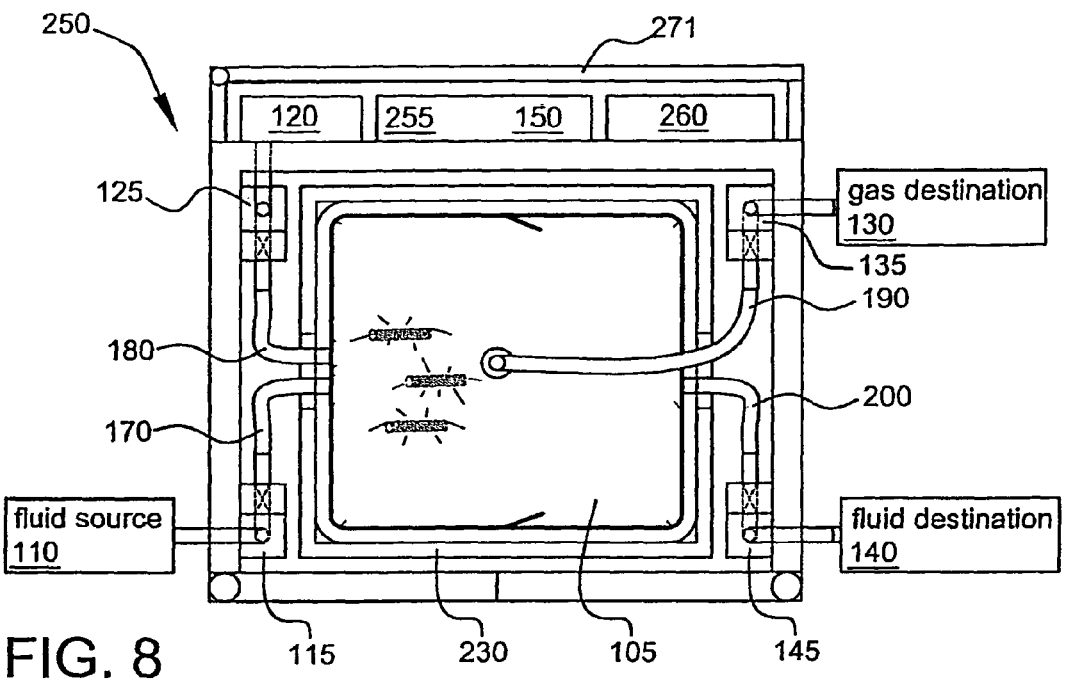
FIG. 8 shows a diagrammatic top view of the bioreactor housing of FIG. 7, in use.

FIG. 8 shows a diagrammatic top view of the bioreactor housing 250 of FIG. 7, in use.

Figure 9:
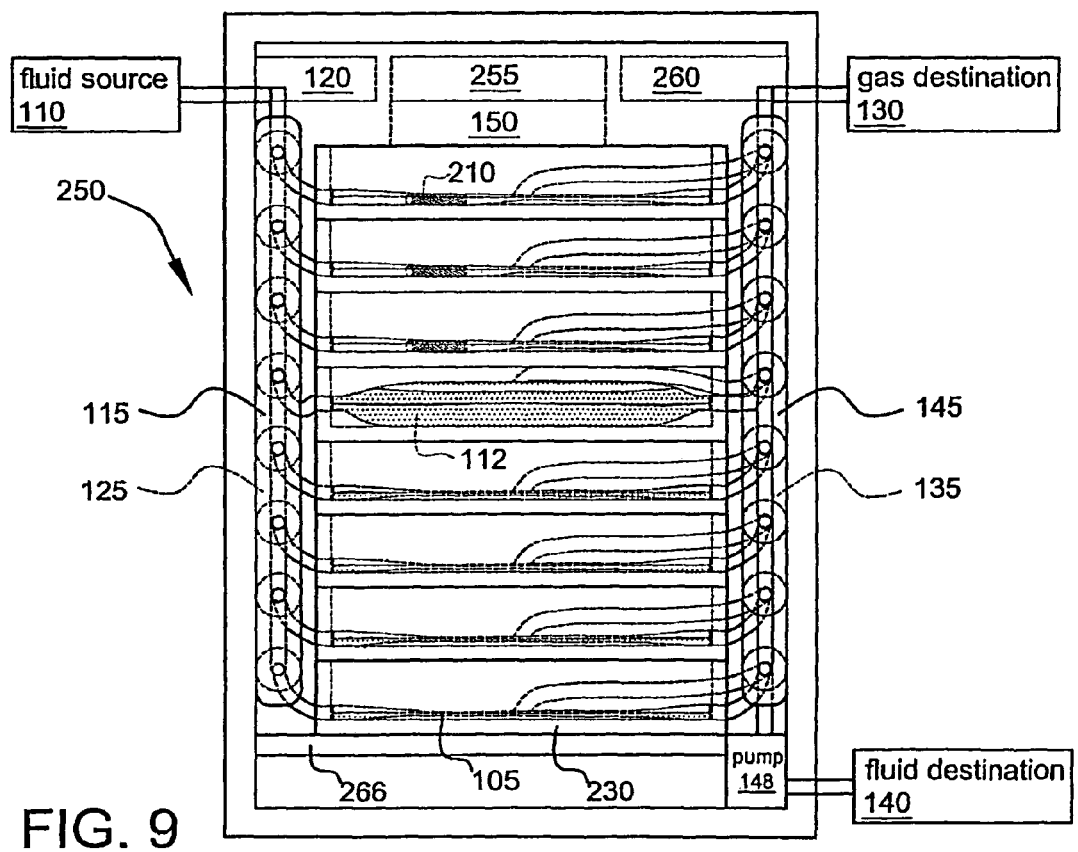
FIG. 9 shows a diagrammatic front view of the bioreactor housing of FIG. 7, in use.

FIG. 9 shows a diagrammatic front view of the bioreactor housing 250 of FIG. 7, in use. Preferably, a stack of bioreactor chambers 105 in containers 230 are installed in housing 250, as shown. Preferably, bioreactor 102 then runs automatically, according to the programming of controller 150, serially incubating and emptying each bioreactor chamber 105 in turn, as shown. Preferably, when every bioreactor chamber 105 in the stack has been used and emptied, the user removes the used bioreactor chambers 105 and installs new bioreactor chambers 105. Upon reading the teachings of this specification, those with ordinary skill in the art will now understand that, under appropriate circumstances, considering such issues as advances in technology, user preference, etc., other arrangements, such as manual operation, incubating multiple bioreactor chambers simultaneously, etc., may suffice.

FIG. 10 shows a cross-sectional view of the bioreactor chamber 105 of FIG. 2 with fluid 112 added, in use. Preferably, gas 122 bubbles into fluid 112 in bag 160 from gas input 180, as shown, disturbing the interface between fluid 112 and headspace 123, as shown, facilitating gas exchange between fluid 112 and headspace 123.

FIG. 11 shows a cross-sectional view of diagrammatic front view of the bioreactor chamber of FIG. 2 with fluid 112 added, in use, with an aerator 187. In an alternate preferred embodiment, gas 122 bubbles into fluid 112 in bag 160 from aerator 187, as shown, disturbing the interface between fluid 112 and headspace 123, as shown, facilitating gas exchange between fluid 112 and headspace 123. Preferably, bioreactor chamber 105 comprises aerator 187, as shown, which comprises a gas diffuser of the sort known in the art of aeration, such as, for example, a reusable steel air manifold, a disposable ceramic fish tank type aerator, a disposable flexible plastic fish tank type aerator (as shown), etc.

FIG. 12 shows a diagram of the path of gas 122 through bioreactor 102. Preferably, gas source 120 comprises an apparatus such as, for example, a gas pump 121, as shown, a compressed gas cylinder, an oxygen generator, etc. Preferably, there is a filter 119 between gas source 120 and gas input manifold 125. Preferably, filter 119 is adapted to filter microbes out of gas 122. Preferably, gas source 120 comprises a source of gas 122 suitable to supporting bioreactions, such as, for example, atmospheric air 124, as shown, nitrogen/oxygen mixtures, pure oxygen, etc. Upon reading the teachings of this specification, those with ordinary skill in the art will now understand that, under appropriate circumstances, considering such issues as advances in technology, user preference, etc., other gas sources, such as remote air pumps, bellows, etc., may suffice.

FIG. 13 shows a diagram of the path of fluid 112 through bioreactor 102.

Figure 14:
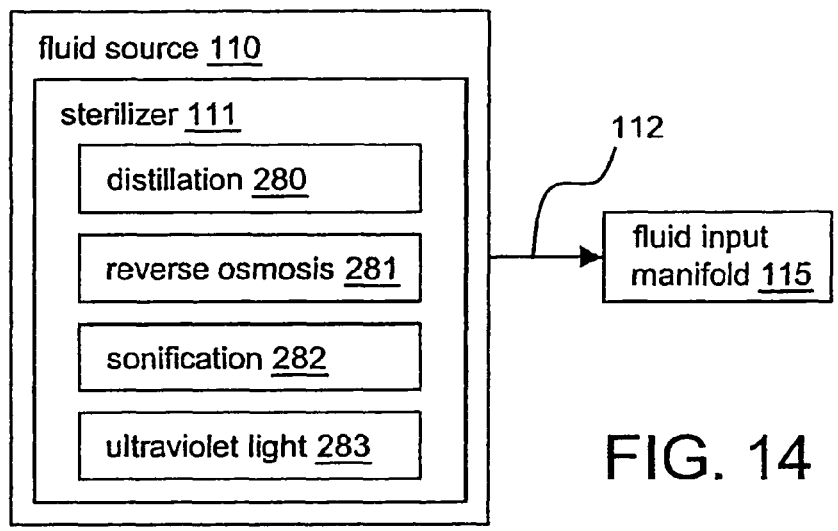
FIG. 14 shows a diagram of fluid pretreatment options.

FIG. 14 shows a diagram of fluid 112 pretreatment options. Preferably, fluid source 110 comprises a source of fluid 112 suitable to supporting bioreactions, preferably a source of sterilized water 114, as shown. Preferably, fluid source 110 comprises a sterilizer 111 such as, for example, a temperature controlled tank, a reverse-osmosis system, a deionization system, etc. Preferably, fluid source 110 is controlled by controller 150, as shown. Upon reading the teachings of this specification, those with ordinary skill in the art will now understand that, under appropriate circumstances, considering such issues as advances in technology, user preference, etc., other fluid sources, such as municipal water pipes, fluid pumped from a container, etc., may suffice, as shown.

Preferably, water 114 is sterilized by sterilizer 111, either in fluid source 110 or by another apparatus prior to reaching fluid input manifold 115, as by at least one of distillation 280, reverse osmosis 281, sonification 282, and/or ultraviolet light treatment 283, as shown. Preferably, where water 114 is turbid (i.e., from a city water supply, from a lake, etc.), sonification 282 and ultraviolet light 283 are used together to provide complete sterilization. Upon reading the teachings of this specification, those with ordinary skill in the art will now understand that, under appropriate circumstances, considering such issues as advances in technology, user preference, etc., other methods of sterilizing water, such as radiation, heat, deionization, chemical treatment, etc., may suffice.

FIG. 15 shows a diagram of fluid 112 output directly into an irrigation system 285. Preferably, fluid destination 140 delivers fluid 112 to the required point of use or storage, as shown. Preferably, fluid destination 140 delivers fluid 112 directly into irrigation system 285, as shown, which then delivers fluid 112 to crops including leaves and stems thereof, soil, etc. Preferably, fluid destination 140 comprises an apparatus such as, for example, a pump, a venturi suction device, a drain into an irrigation water tank, etc. Preferably, fluid destination 140 is controlled by controller 150, as shown. Upon reading the teachings of this specification, those with ordinary skill in the art will now understand that, under appropriate circumstances, considering such issues as advances in technology, user preference, etc., other fluid outputs, such as a fluid storage device, a freezer, etc., may suffice.

Preferably, where live microbes 101 comprise soil bacteria, live microbes 101 are protected from light (especially ultraviolet light) by irrigating at night. Preferably, the live microbe 101 contents of one incubated 30-gallon bioreactor chamber 105 are added to irrigation water to treat about four hundred acres of crops or turf, typically on an about weekly basis. Preferably, a single bioreactor chamber 105 may be used over multiple days until it is emptied, depending of the amount of time it takes to irrigate four hundred acres. Upon reading the teachings of this specification, those with ordinary skill in the art will now understand that, under appropriate circumstances, considering such issues as advances in technology, user preference, etc., other treatment levels, such as daily, monthly, yearly, higher concentration of application, lower concentration of application, etc., may suffice.

Figure 16:
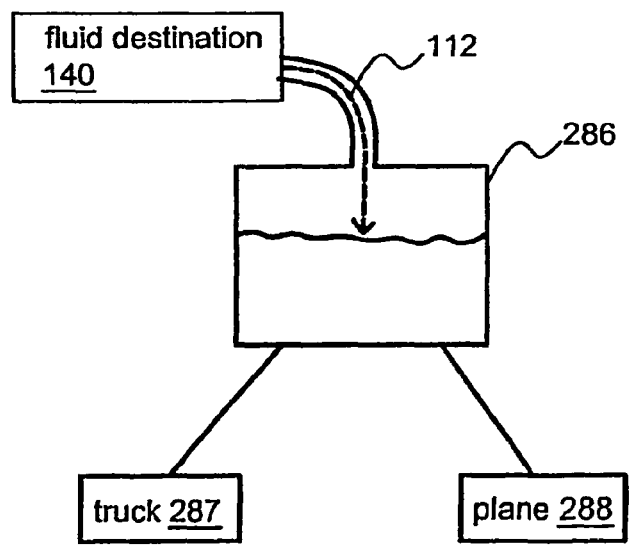
FIG. 16 shows a diagram of fluid output into other destinations.

FIG. 16 shows a diagram of fluid 112 output into other destinations. Preferably, fluid destination 140 delivers fluid 112 to an irrigation tank 286, on, for example, a sprayer truck 287, a sprayer airplane 288, etc, as shown. Upon reading the teachings of this specification, those with ordinary skill in the art will now understand that, under appropriate circumstances, considering such issues as advances in technology, user preference, etc., other fluid destinations, such as watering cans, irrigation ponds, etc., may suffice.

Figure 17:
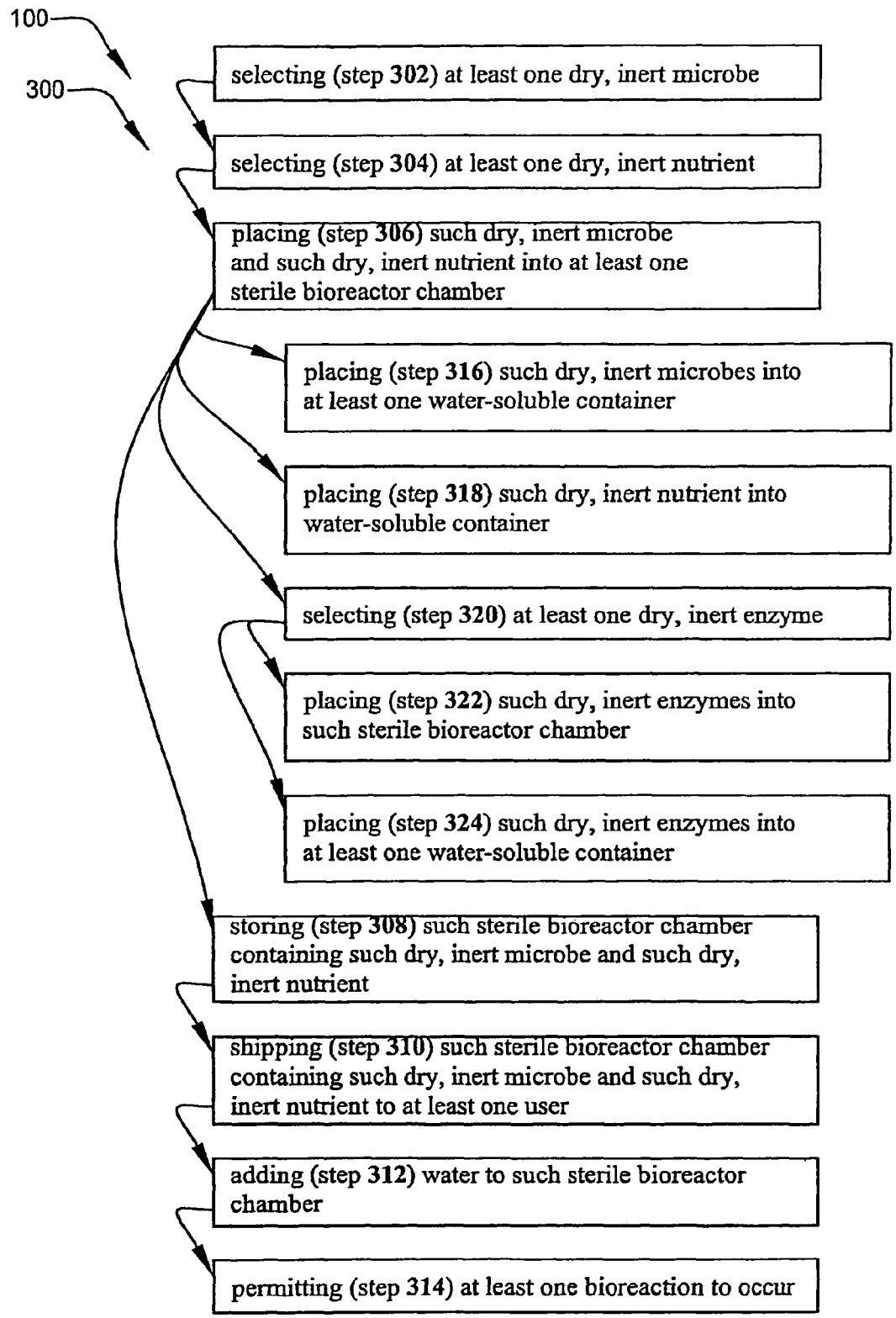
FIG. 17 shows a diagram of a method of manufacturing bioreactor chambers according to a preferred embodiment of the present invention.

FIG. 17 shows a diagram of a method 300 of manufacturing bioreactor chambers 105 according to a preferred embodiment of the present invention. Preferably, bioreactor system 100 comprises method 300, as shown. Preferably, method 300 comprises the steps of: selecting (step 302) at least one dry, inert microbe 210; selecting (step 304) at least one dry, inert nutrient 215 adapted to support the life of such dry, inert microbe 210; placing (step 306) such dry, inert microbe 210 and such dry, inert nutrient 215 into at least one sterile bioreactor chamber 105; and storing (step 308) such sterile bioreactor chamber 105 containing such dry, inert microbe 210 and such dry, inert nutrient 215, as shown. Upon reading the teachings of this specification, those with ordinary skill in the art will now understand that, under appropriate circumstances, considering such issues as advances in technology, user preference, etc., other steps, such as sterilizing the bioreactor chamber prior to placing the microbes inside, closing the inputs and outputs to maintain sterility, packaging the loaded bioreactor chamber in a sterile container, etc., may suffice.

Preferably, method 300 further comprises the step of shipping (step 310) such sterile bioreactor chamber 105 containing such dry, inert microbe 210 and such dry, inert nutrient 215 to at least one user, as shown. Upon reading the teachings of this specification, those with ordinary skill in the art will now understand that, under appropriate circumstances, considering such issues as advances in technology, user preference, etc., other steps, such as accepting an order for a preloaded bioreactor, receiving a promise of payment for the preloaded bioreactor, setting up automatic timed shipments of preloaded bioreactors, etc., may suffice.

Preferably, method 300 further comprises the steps of: adding (step 312) water 114 to such sterile bioreactor chamber 105 containing such dry, inert microbe 210 and such dry, inert nutrient 215; and permitting (step 314) at least one bioreaction to occur, as shown.

Preferably, method 300 further comprises the step of placing (step 316) such dry, inert microbes 210 into at least one water-soluble container 225 prior to placing (step 306) such dry, inert microbes 210 into such sterile bioreactor chamber 105, as shown. Preferably, dry, inert microbes 210 are packaged into water-soluble containers 225 in a sterile environment. Preferably, the filled water-soluble containers 225 are inserted into bioreactor chamber 105 in a sterile environment, such as, for example, a cleanroom, a laboratory, etc. Preferably, the filled water-soluble containers 225 are inserted into bioreactor chamber 105 through at least one of fluid input 170, gas input 180, gas output 190, and fluid output 200. Upon reading the teachings of this specification, those with ordinary skill in the art will now understand that, under appropriate circumstances, considering such issues as advances in technology, user preference, etc., other methods of loading dry, inert microbes into the bioreactor chambers, such as a separate sealable port in the bioreactor chamber, manufacturing the bioreactor chambers with the dry, inert microbes already inside, manufacturing the bioreactor chambers with a water-soluble film compartment containing the dry, inert microbes, etc., may suffice.

Preferably, method 300 further comprises the step of placing (step 318) such dry, inert nutrient 215 into water-soluble container 225 prior to placing (step 306) such dry, inert nutrient 215 into such sterile bioreactor chamber 105, as shown.

Preferably, method 300 further comprises the steps of: selecting (step 320) at least one dry, inert enzyme 220 adapted to support the life of such dry, inert microbe 210; and placing (step 322) such dry, inert enzymes 220 into such sterile bioreactor chamber 105, as shown. Preferably, method 300 further comprises the step of placing (step 324) such dry, inert enzymes 220 into at least one water-soluble container 225 prior to placing (step 322) such dry, inert enzymes 220 into such sterile bioreactor chamber 105, as shown.

Figure 18:
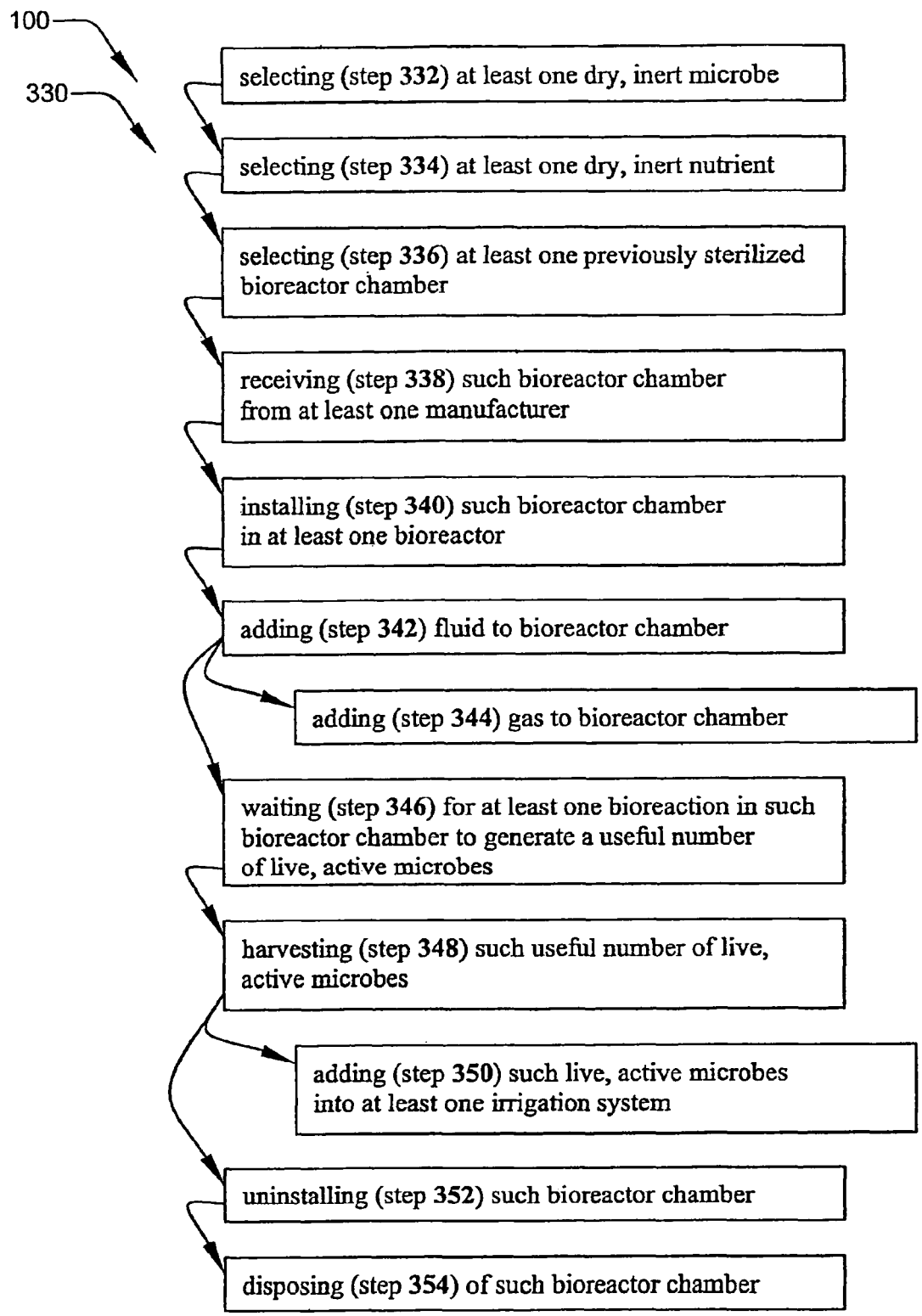
FIG. 18 shows a diagram of a method of using bioreactor chambers according to a preferred embodiment of the present invention.

FIG. 18 shows a diagram of a method 330 of using bioreactor chambers 105 according to a preferred embodiment of the present invention. Preferably, bioreactor system 100 comprises method 330, as shown. Preferably, method 330 comprises the steps of: selecting (step 332) at least one dry, inert microbe 210; selecting (step 334) at least one dry, inert nutrient 215 adapted to support the life of such dry, inert microbe 210; selecting (step 336) at least one previously sterilized bioreactor chamber 105; receiving (step 338) such bioreactor chamber 105 containing such dry, inert microbe 210 and such dry, inert nutrient 215 from at least one manufacturer; installing (step 340) such bioreactor chamber 105 containing such dry, inert microbe 210 and such dry, inert nutrient 215 in at least one bioreactor 102; adding (step 342) fluid 112 (i.e. water 114) to such bioreactor chamber 105 containing such dry, inert microbe 210 and such dry, inert nutrient 215; waiting (step 346) for at least one bioreaction in such bioreactor chamber 105 to generate a useful number of live, active microbes 101; and harvesting (step 348) such useful number of live, active microbes 101, as shown.

Preferably, method 330 further comprises the step of adding (step 344) oxygen (i.e. gas 122) to such bioreactor chamber 105, after such step of adding (step 342) fluid 112 to such bioreactor chamber 105, as shown.

Preferably, the step of harvesting (step 348) such useful number of live, active microbe 101 comprises the step of adding (step 350) such useful number of live, active microbes 101 into at least one irrigation system 285, as shown.

Preferably, method 330 further comprises the steps of: uninstalling (step 352) such bioreactor chamber 105; and disposing (step 354) of such bioreactor chamber 105, after the step of harvesting (step 348) such useful number of live, active microbes 101, as shown.

An example of the use of controller 150 to several of the steps of method 330 is described here. To prepare a single batch of live microbes 101, having an eight-hour incubation period, to dispense into irrigation system 285 at midnight, the following timed sequence may be used (all valves start closed):

| | | |
|---|---|---|
| 4:00 pm | Open one valve 117 on fluid input manifold 115 | Adds fluid 112 to one bioreactor chamber 105 |
| 4:00 pm | Open one valve 127 on gas input manifold 125 | Adds gas to same bioreactor chamber 105 |
| 4:00 pm | Open one valve 137 on gas output manifold 135 | Releases gas 122 from same bioreactor chamber 105, rate controlled by gas relief valve 138 |
| 4:30 pm | Close valve 117 on fluid input manifold 115 | Shuts off fluid 112 going to same bioreactor chamber 105 (timed to add about 30 gallons) |
| 12:00 am | Open valve 147 on fluid output manifold 145 | Releases fluid 112 with live microbes 101 from same bioreactor chamber 105 into fluid output manifold 145 |
| 12:00 am | Activate pump 148 at programmed flow rate | Moves fluid 112 from fluid output manifold 145 to fluid destination 140 |
| 12:00 am | Close same valve 127 on gas input manifold 125 | Shuts off gas 122 to same bioreactor 105 |

To prepare a two batches of live microbes 101, having an eight-hour incubation period, to dispense 30 gallons of fluid 112 into irrigation system 285 at midnight for three nights, the following timed sequence may be used (all valves start closed) according to an exemplary sequence in which microbes are growing/reacting in a second bioreactor chamber while previously reacted/grown microbes are being discharged from a first bioreactor chamber via a manifold:

| Time | Action | Result |
|---|---|---|
| 4:00 pm 1st day | Open first valve 117 on fluid input manifold 115 | Adds fluid 112 to first bioreactor chamber 105 |
| 4:00 pm 1st day | Open first valve 127 on gas input manifold 125 | Adds gas to first bioreactor chamber 105 |
| 4:00 pm 1st day | Open first valve 137 on gas output manifold 135 | Releases gas 122 from first bioreactor chamber 105, rate controlled by gas relief valve 138 |
| 4:30 pm 1st day | Close first valve 117 on fluid input manifold 115 | Shuts off fluid 112 going to first bioreactor chamber 105 (timed to add about 45 gallons) |
| 12:00 am 1st day | Open first valve 147 on fluid output manifold 145 | Releases fluid 112 with live microbes 101 from first bioreactor chamber 105 into fluid output manifold 145 |
| 12:00 am 1st day | Activate pump 148 at programmed flow rate | Moves 30 gallons of fluid 112 from fluid output manifold 145 to fluid destination 140 |
| 12:20 am 1st day | Deactivate pump 148 | Timed to leave 15 gallons of fluid 112 in first bioreactor 105 |
| 4:00 pm 2nd day | Open second valve 117 on fluid input manifold 115 | Adds fluid 112 to second bioreactor chamber 105 |
| 4:00 pm 2nd day | Open second valve 127 on gas input manifold 125 | Adds gas to second bioreactor chamber 105 |
| 4:00 pm 2nd day | Open second valve 137 on gas output manifold 135 | Releases gas 122 from second bioreactor chamber 105, rate controlled by gas relief valve 138 |
| 4:30 pm 2nd day | Close second valve 117 on fluid input manifold 115 | Shuts off fluid 112 going to second bioreactor chamber 105 (timed to add about 45 gallons) |
| 12:00 am 2nd day | Activate pump 148 at programmed flow rate | Moves 15 gallons of fluid 112 from fluid output manifold 145 to fluid destination 140 (from first bioreactor 105) |
| 12:00 am 2nd day | Close first valve 127 on gas input manifold 125 | Shuts off gas 122 to first bioreactor 105 |
| 12:10 am 2nd day | Open second valve 147 on fluid output manifold 145 | Releases fluid 1!2 with live microbes 101 from second bioreactor chamber 105 into fluid output manifold 145 (first bioreactor is empty) |
| 12:10 am 2nd day | Continue pump 148 at programmed flow rate | Moves 15 gallons of fluid 112 from fluid output manifold 145 to fluid destination 140 (from second bioreactor 105) |
| 12:20 am 2nd day | Deactivate pump 148 | Timed to leave 30 gallons of fluid 112 in second bioreactor 105 |
| 12:00 am 3rd day | Activate pump 148 at programmed flow rate | Moves 30 gallons of fluid 112 from fluid output manifold 145 to fluid destination 140 (from second bioreactor 105) |
| 12:00 am 3rd day | Close second valve 127 on gas input manifold 125 | Shuts off gas 122 to second bioreactor 105 |
| 12:20 am 3rd day | Deactivate pump 148 | Second bioreactor 105 is empty |

Figure 19:
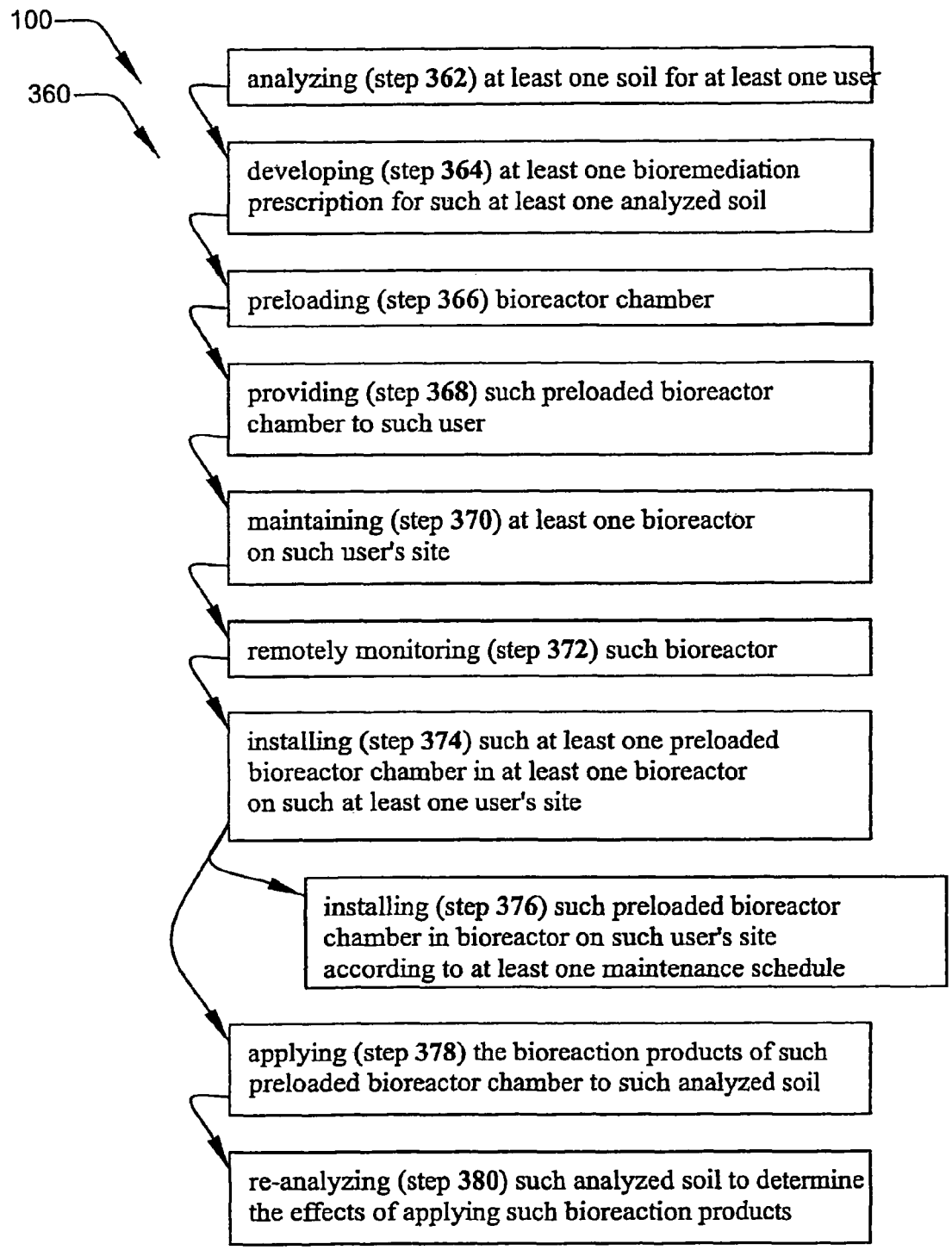
FIG. 19 shows a diagram of a method of distributing bioreactor chambers according to a preferred embodiment of the present invention.

FIG. 19 shows a diagram of a method 360 of distributing bioreactor chambers 105 according to a preferred embodiment of the present invention. Preferably, bioreactor system 100 comprises method 360, as shown. Preferably, method 360 comprises the steps of: analyzing (step 362) at least one soil for at least one user; developing (step 364) at least one bioremediation prescription 365 for such at least one analyzed soil; preloading (step 366) at least one bioreactor chamber 105 with dry, inert microbes 210 according to such bioremediation prescription 365; and providing (step 368) such preloaded bioreactor chamber 105 to such user, as shown.

Preferably, method 330 further comprises the step of maintaining (step 370) at least one bioreactor 102 on such user's site, as shown.

Preferably, method 330 further comprises the step of remotely monitoring (step 372) such bioreactor 102, as shown.

Preferably, method 330 further comprises the step of replacing the at least one bioreaction chamber that was uninstalled (step 352) and disposed (step 354) by installing (step 374) such at least one preloaded bioreactor chamber 105 in at least one bioreactor 102 on such at least one user's site, as shown.

Preferably, method 330 further comprises the step of installing (step 376) such preloaded bioreactor chamber 105 in at least one bioreactor 102 on such user's site according to at least one maintenance schedule 377, as shown.

Preferably, method 330 further comprises the step of applying (step 378) the bioreaction products (i.e. live microbes 101) of such preloaded bioreactor chamber 105 to such analyzed soil, as shown.

Preferably, method 330 further comprises the step of re-analyzing (step 380) such analyzed soil to determine the effects of applying such bioreaction products (i.e. live microbes 101), as shown.

Preferably, bioremediation prescription 365 comprises a bioremediation plan adapted to improve soil quality, to improve plant health, and to control pathogens, including such aspects as, for example: type and frequency of microbial additions to the irrigation water; type and frequency of fertilizer use; type and frequency of fungicide use; type and frequency of pesticide use; use of chitin to stimulate plant immune system responses to fungi; use of cover crops; use of crop rotation; sound stimulation of the plants; seed coating and pretreatments; etc. Typically, a bioremediation plan is developed by one skilled in the art of bioremediation, organic farming, farming, microbiology, plant biology, etc, as shown. Upon reading the teachings of this specification, those with ordinary skill in the art will now understand that, under appropriate circumstances, considering such issues as advances in technology, user preference, etc., other bioremediation prescription aspects, such as amendments to change the soil structure, amendments to change the soil pH, soil sterilization by oxidation, addition of micronutrients, soil fumigation, biofumigation by green manures, bioaccumulation of radioactive particles, etc., may suffice.

Preferably, maintenance schedule 377 comprises the schedule on which the user (preferably a bioreactor maintenance contractor) or the end-user (preferably a farmer or turf manager) replaces used bioreactor chambers 105 (and preferably sterilizes housing 250).

Preferably, bioreactor chambers 105 are replaced after all of the bioreactor chambers 105 in all of the installed housings 250 are used. This schedule will depend on such factors as, for example, the number of housings 250 in use; the number of bioreactor chambers 105 in each housing 250; the bioreaction time for the species of microbe being used; the frequency of using bioreaction chambers 105; the speed of emptying live microbes 101 from bioreaction chambers 105 into the irrigation system 285; etc. Typically, maintenance schedule 377 will require bioreactor chambers 105 to be replaced about weekly.

Figure 20:
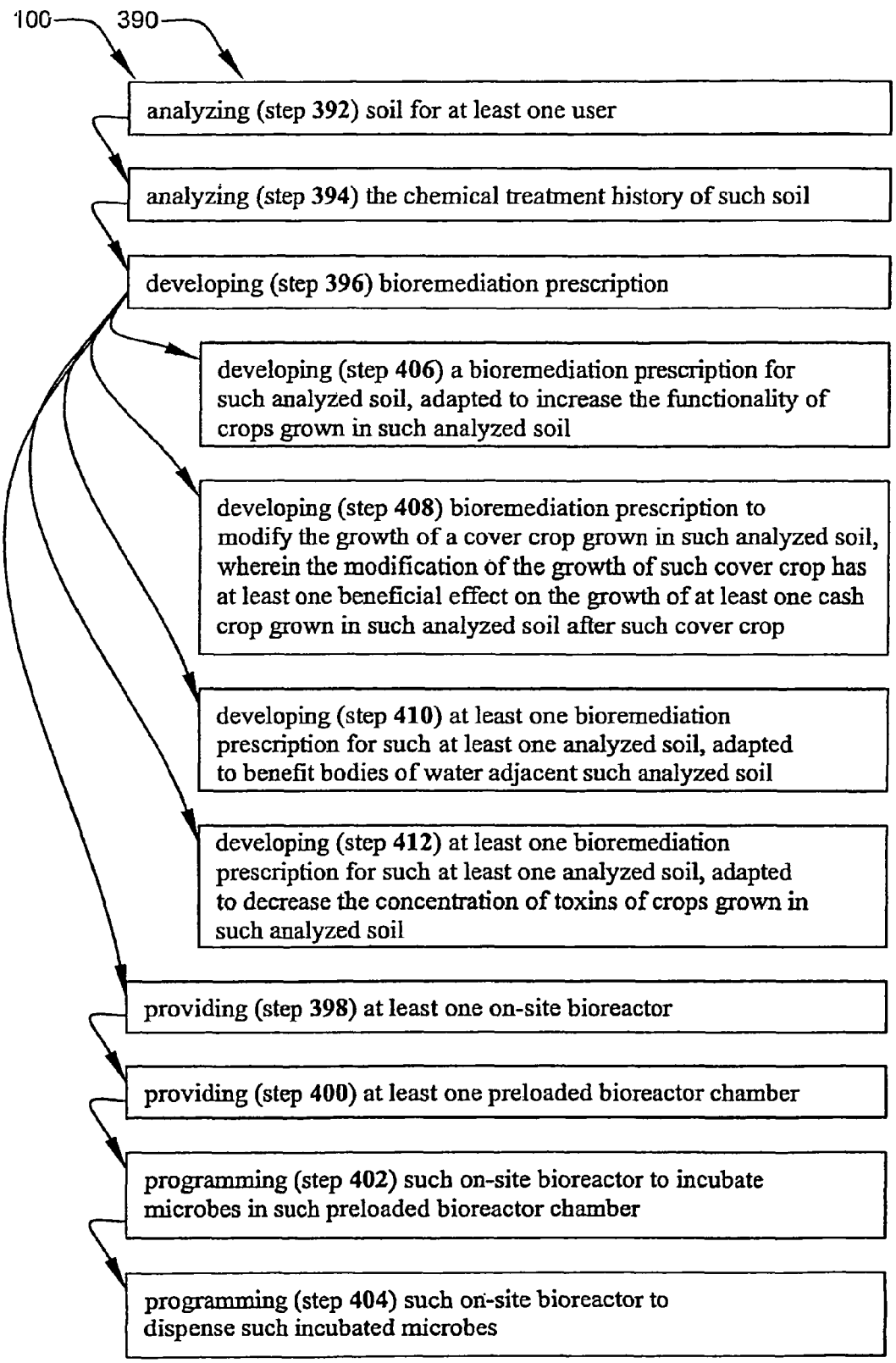
FIG. 20 shows a diagram of a method of farming using bioreactor chambers according to a preferred embodiment of the present invention.

FIG. 20 shows a diagram of a method 390 of farming using bioreactor chambers 105 according to a preferred embodiment of the present invention. Preferably, bioreactor system 100 comprises method 390, as shown. Preferably, method 390 comprises the steps of: analyzing (step 392) at least one soil for at least one user; analyzing (step 394) at least one chemical treatment history of such soil; developing (step 396) at least one bioremediation prescription 365 for such analyzed soil; providing (step 398) at least one on-site bioreactor 102; providing (step 400) at least one preloaded bioreactor chamber 105 containing inert microbes 210, according to such bioremediation prescription 365, adapted to be used with such on-site bioreactor 102; programming (step 402) such on-site bioreactor 102 to incubate such microbes 210 in such preloaded bioreactor chamber 105; and programming (step 404) such on-site bioreactor 102 to dispense such incubated microbes 210 (i.e. live microbes 101), as shown. Programming controller 150 to open and close solenoid valves in bioreactor 102 on a timed schedule can be done by one of ordinary skill in the art.

Preferably, method 390 further comprises the step of developing (step 406) at least one bioremediation prescription 365 for such at least one analyzed soil, adapted to increase the functionality of crops grown in such analyzed soil, as shown. Functional crops are crops having proven enhanced nutrient content providing proven health benefits, as is known in the art of agriculture. For example, an onion grown in specially bacterially treated soil to have an enhanced calcium content, where calcium is known to help prevent bone loss in women, is a functional food created by applying bioremediation techniques to the soil.

Preferably, method 390 further comprises the step of developing (step 408) at least one bioremediation prescription 365 for such analyzed soil, adapted to modify the growth of at least one cover crop grown in such at least one analyzed soil, wherein the modification of the growth of such cover crop has at least one beneficial effect on the growth of at least one cash crop grown in such analyzed soil after such cover crop, as shown. Cover crops are crops grown on soil, usually in the off-season, to preserve and improve the soil, as is known in the art of agriculture. Cover crops are typically turned under the soil to act as a green manure, prior to the cash crop being sown. For example, treating a cover crop of clover with nitrogen-fixing bacteria will result in enhanced growth of the cash crop planted afterward due to nitrogen-enrichment of the soil.

Preferably, method 390 further comprises the step of developing (step 410) at least one bioremediation prescription 365 for such at least one analyzed soil, adapted to benefit bodies of water adjacent such analyzed soil, as shown. For example, a microbe may be selected that, in addition to suppressing pathogens in soil, will suppress pathogens in lakes and ponds which receive run-off from the treated soil.

Preferably, method 390 further comprises the step of developing (step 412) at least one bioremediation prescription 365 for such at least one analyzed soil, adapted to decrease the concentration of toxins of crops grown in such analyzed soil, as shown. For example, mycotoxins and aflatoxins are types of harmful (poisonous and carcinogenic) fungal metabolites that some fungi generate in response to stress, which contaminate food crops hosting the fungi. Mycotoxin concentrations in crops may increase sharply when chemical fungicides are applied to the crops. However, inoculating crops with certain bacteria (such as, for example, *Bacillus pumilus*) inhibits mycotoxin production by fungi, decreasing the concentration of mycotoxin contaminating the food crop.

Figure 21:
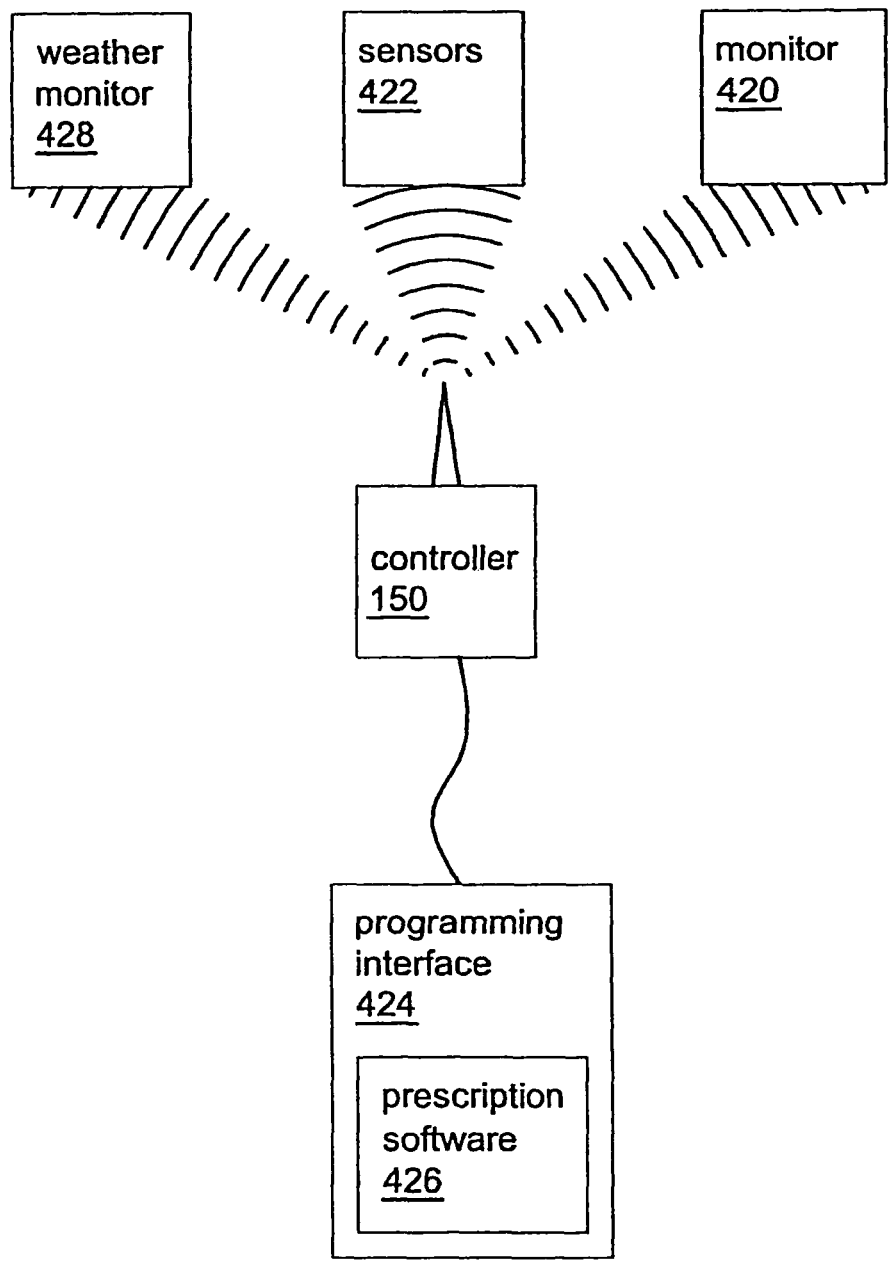
FIG. 21 shows a diagram of additional interfaces to the controller.

FIG. 21 shows a diagram of additional interfaces to controller 150 beyond the ones previously described. Preferably, bioreactor system 100 further comprises at least one of monitor 420, sensors 422, weather monitor 428, programming interface 424, and prescription software 426, which preferably interface with controller 150. Upon reading the teachings of this specification, those with ordinary skill in the art will now understand that, under appropriate circumstances, considering such issues as advances in technology, user preference, etc., other controller interfaces, such as light controls, other temperature controls, irrigation system controls, alarms, etc., may suffice.

Preferably, monitor 420 comprises a remote monitoring computer system which receives data at least about the status of bioreactor 102, such as, for example, the number of bioreactor chambers 105 remaining, error warnings, housing 250 temperature, gas 122 pressure, sensor data, etc. Preferably, monitor 420 is remote from bioreactor 102, preferably at the user's office, more preferably at the bioreactor maintenance contractor's location. Preferably, monitor 420 may be used to remotely control and/or program at least bioreactor 102. Upon reading the teachings of this specification, those with ordinary skill in the art will now understand that, under appropriate circumstances, considering such issues as advances in technology, user preference, etc., other monitor arrangements, such as other data inputs, other data outputs, etc., may suffice.

Preferably, sensors 422 comprise sensors at the end-user's site, such as, for example, soil moisture sensors, soil temperature sensors, air temperature sensors, weather monitor 428, etc. Preferably, weather monitor 428 monitors and records weather conditions as is known in the art of weather stations. Preferably, the data from sensors 422 is transmitted to at least one of controller 150, prescription software 426, and/or monitor 420. Upon reading the teachings of this specification, those with ordinary skill in the art will now understand that, under appropriate circumstances, considering such issues as advances in technology, user preference, etc., other sensors, such as soil pH, soil nitrogen content, soil oxygen content, solar intensity, etc., may suffice.

Preferably, at least one of monitor 420, sensors 422, and weather monitor 428 are wirelessly connected to controller 150, by means such as, for example, radio, wireless internet connection, cellular phone technology, etc. Upon reading the teachings of this specification, those with ordinary skill in the art will now understand that, under appropriate circumstances, considering such issues as advances in technology, user preference, etc., other data connections, such as satellite uplinks, data cables, optical data transmission, etc., may suffice.

Preferably, programming interface 424 comprises a user interface with controller 150 to permit monitoring, controlling, and/or programming controller 150. Preferably, programming interface 424 comprises means such as, for example, a computer integral with housing 250, a separate computer with a data cable connected to controller 150, a monitor and keyboard connected directly to programming interface 424, a wireless computer connection to controller 150, etc.

Preferably, prescription software 426 comprises software adapted to receive input about soil conditions, crop types, weather conditions, etc, and to provide a bioremediation prescription 365 in response to the provided data. Preferably, prescription software 426 is stored in programming interface 424. Preferably, prescription software 426 is adapted to use data from sensors 422, weather monitor 428, monitor 420, programming interface 424, the user, the end-user, etc. Upon reading the teachings of this specification, those with ordinary skill in the art will now understand that, under appropriate circumstances, considering such issues as advances in technology, user preference, etc., other prescription software locations, such as at the remote monitoring computer, on the internet, on a home computer, on another type of computer processor, etc., may suffice.

The preceding merely illustrates the principles of the invention. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

This description of the exemplary embodiments is intended to be read in connection with the figures of the accompanying drawing, which are to be considered part of the entire written description. In the description, relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

Embodiments

Live microbes 101 at least embody herein wherein such at least one microbe comprises at least one bacteria.

Bioreactor chamber 105 at least embodies herein at least one bioreactor container adapted to contain at least one bioreaction; and at least embodies herein wherein such at least one microbe is stored within such at least one bioreactor container; and at least embodies herein wherein such at least one nutrient is stored within such at least one bioreactor container; and at least embodies herein wherein such at least one enzyme is stored within such at least one bioreactor container; and at least embodies herein wherein such at least one bioreactor container comprises at least one flexible container; and at least embodies herein wherein at least one interior of such at least one bioreactor container, containing such at least one microbe, is sterile of pathogens; and at least embodies herein at least one flexible container adapted to flexibly contain at least one fluid containing at least one cell culture; and at least embodies herein wherein such at least one flexible container has a volume of about 30 gallons; and at least embodies herein wherein such at least one flexible container is opaque; and at least embodies herein wherein about 400 acres of crops are treated per 30 gallon flexible container; and at least embodies herein bioreactor container means for containing at least one bioreaction; and at least embodies herein wherein such microbe means is stored within such bioreactor container means; and at least embodies herein wherein such bioreactor container means comprises at least one flexible container; and at least embodies herein flexible container means for flexibly containing at least one fluid containing at least one cell culture.

Fluid source 110 at least embodies herein at least one fluid source adapted to provide at least one source of at least one fluid.

Fluid 112 at least embodies herein wherein such at least one fluid comprises temperature-controlled water.

Sterilized water 114 at least embodies herein such at least one fluid, and wherein such at least one fluid comprises sterilized water.

Fluid input manifold 115 at least embodies herein at least one fluid input manifold adapted to provide at least one fluid to such at least one fluid input.

Gas source 120 at least embodies herein at least one gas source adapted to provide at least one source of gas to such at least one gas input manifold.

Gas input manifold 125 at least embodies herein one gas input manifold adapted to provide gas to such at least one gas input.

Gas output manifold 135 at least embodies herein at least one gas output manifold adapted to receive gas from such at least one gas output.

Fluid destination 140 at least embodies herein at least one irrigation system input adapted to input such fluid output from such at least one flexible container into such at least one irrigation system.

Fluid output manifold 145 at least embodies herein at least one fluid output manifold adapted to receive fluid from such at least one fluid output.

Controller 150 at least embodies herein at least one controller adapted to control the contents of such at least one flexible container; and at least embodies herein wherein such at least one controller controls the flow of fluid from such at least one fluid source to such at least one fluid input manifold; and at least embodies herein wherein such at least one controller controls the flow of fluid from such at least one fluid input manifold to such at least one fluid input; and at least embodies herein wherein such at least one controller controls the flow of fluid from such at least one fluid output to such at least one fluid output manifold; and at least embodies herein wherein such at least one controller controls the flow of fluid from such at least one fluid output manifold to at least one fluid destination. In this manner, by controlling fluid flow in and out of the at least one flexible container, controller 150 effectively selects which of the at least one flexible container(s) are utilized. Controller 150 also at least embodies herein wherein such at least one controller controls the flow of gas from such at least one gas source to such at least one gas input manifold; and at least embodies herein wherein such at least one controller controls the flow of gas from such at least one gas input manifold to such at least one gas input; and at least embodies herein wherein such at least one controller controls the flow of gas from such at least one gas output to such at least one gas output manifold; and at least embodies herein wherein such at least one controller controls the flow of gas from such at least one gas output manifold to at least one gas destination; and at least embodies herein wherein such at least one controller comprises at least one programmable irrigation timer; and at least embodies herein controller means for controlling the contents of such flexible container means.

Fluid input 170 at least embodies herein at least one fluid input adapted to input fluid into such at least one flexible container; and at least embodies herein fluid input means for inputting fluid into such flexible container means.

Filter 175 at least embodies herein wherein such at least one fluid input comprises at least one filter.

One-way valve 176 at least embodies herein wherein such at least one fluid input comprises at least one one-way valve.

Gas input 180 at least embodies herein at least one gas input adapted to input at least one gas into such at least one flexible container; and at least embodies herein wherein such at least one gas input is adapted to create bubbles in such at least one fluid; and at least embodies herein gas input means for inputting at least one gas into such flexible container means, wherein such gas input means is adapted to create bubbles in such at least one aqueous solution.

Filter 185 at least embodies herein wherein such at least one gas input comprises at least one filter.

One-way valve 186 at least embodies herein wherein such at least one gas input comprises at least one one-way valve.

Aerator 187 at least embodies herein wherein such at least one gas input comprises at least one aerator.

Gas output 190 at least embodies herein at least one gas output adapted to output at least one gas from such at least one flexible container; and at least embodies herein gas output means for outputting at least one gas from such flexible container means.

Filter 195 at least embodies herein wherein such at least one gas output comprises at least one filter.

One-way valve 196 at least embodies herein wherein such at least one gas output comprises at least one one-way valve.

Fluid output 200 at least embodies herein at least one fluid output adapted to output fluid from such at least one flexible container; and at least embodies herein fluid output means for outputting fluid from such flexible container means.

One-way valve 206 at least embodies herein wherein such at least one fluid output comprises at least one one-way valve.

Inert microbes 210 at least embody herein at least one microbe adapted to provide at least one living microbe, wherein such at least one microbe may be in an inert, dry state; and at least embodies herein microbe means for providing at least one living microbe, wherein such microbe means is in an inert state. Inert microbes 210 may alternatively be in other states, such as wet.

Dry, inert nutrient 215 at least embodies herein at least one nutrient adapted to provide at least one nutrient adapted to support the life of such at least one at least one microbe, wherein such at least one at least one nutrient is in an inert, dry state.

Dry, inert enzymes 220 at least embody herein at least one enzyme adapted to provide at least one enzyme adapted to support the life of such at least one at least one microbe, wherein such at least one at least one enzyme is in an inert, dry state.

Water-soluble capsules 225 at least embody herein at least one first water-soluble container adapted to contain such at least one microbe in at least one water-soluble container; and at least embodies herein at least one second water-soluble container adapted to contain such at least one nutrient in at least one water-soluble container; and at least embodies herein at least one third water-soluble container adapted to contain such at least one enzyme in at least one water-soluble container.

Containers 230 at least embody herein at least one rigid stackable container adapted to provide at least one rigid stackable container adapted to hold such at least one flexible container.

Housing 250 at least embodies herein at least one enclosure adapted to enclose at least such at least one flexible container; and at least embodies herein wherein such at least one enclosure maintains such at least one flexible container at least one selected temperature; and at least embodies herein wherein such at least one enclosure comprises at least one fluid input manifold adapted to provide fluid to such at least one fluid input; and at least embodies herein wherein such at least one enclosure comprises at least one fluid output manifold adapted to receive fluid from such at least one fluid output; and at least embodies herein wherein such at least one enclosure comprises at least one gas input manifold adapted to provide gas to such at least one gas input; and at least embodies herein wherein such at least one enclosure comprises at least one gas output manifold adapted to receive gas from such at least one gas output; and at least embodies herein wherein such at least one enclosure comprises at least one controller adapted to control the contents of such at least one flexible container; and at least embodies herein at least one enclosure adapted to enclose such at least two bioreactor chambers; and at least embodies herein wherein such at least one enclosure is thermally insulated; and at least embodies herein wherein such at least one enclosure comprises at least one temperature control adapted to control at least one temperature within such at least one enclosure; and at least embodies herein wherein such at least one enclosure comprises at least one fluid input manifold adapted to provide at least one fluid to each of such at least two bioreactor chambers; and at least embodies herein wherein such at least one enclosure comprises at least one fluid output manifold adapted to receive fluid from each of such at least two bioreactor chambers; and at least embodies herein wherein such at least one enclosure comprises at least one gas input manifold adapted to provide gas to each of such at least two bioreactor chambers; and at least embodies herein wherein such at least one enclosure comprises at least one gas output manifold adapted to receive gas from each of such at least two bioreactor chambers; and at least embodies herein wherein such at least one enclosure comprises at least one controller adapted to control such at least one temperature control, such at least one fluid input manifold, such at least one fluid output manifold, such at least one gas input manifold, and such at least one gas output manifold; and at least embodies herein enclosure means for enclosing at least such flexible container means; and at least embodies herein enclosure means for enclosing such at least two bioreactor chambers; and at least embodies herein wherein such enclosure means is thermally insulated; and at least embodies herein wherein such enclosure means comprises temperature control means for controlling at least one temperature within such enclosure means; and at least embodies herein wherein such enclosure means comprises fluid input manifold means for providing at least one fluid to each of such at least two bioreactor chambers; and at least embodies herein wherein such enclosure means comprises fluid output manifold means for receiving fluid from each of such at least two bioreactor chambers; and at least embodies herein wherein such enclosure means comprises gas input manifold means for providing gas to each of such at least two bioreactor chambers; and at least embodies herein wherein such enclosure means comprises gas output manifold means for receiving gas from each of such at least two bioreactor chambers; and at least embodies herein wherein such enclosure means comprises controller means for controlling such temperature control means, such fluid input manifold means, such fluid output manifold means, such gas input manifold means, and such gas output manifold means.

Reverse osmosis 281 at least embodies herein wherein such sterilized water is sterilized by reverse osmosis treatment.

Ultraviolet light system 283 at least embodies herein wherein such sterilized water is sterilized with ultraviolet radiation treatment.

Irrigation system 285 at least embodies herein at least one irrigation system adapted to irrigating at least one crop; and at least embodies herein irrigation system means for irrigating at least one crop.

Selecting 302 at least one inert microbe 210 at least embodies herein the step of selecting at least one inert microbe.

Selecting 304 at least one dry, inert nutrient 215 at least embodies herein the step of selecting at least one dry, inert nutrient adapted to support the life of such at least one inert microbe.

Placing 306 microbe 210 and nutrient 215 into bioreactor chamber 105 at least embodies herein the step of placing such at least one dry, inert microbe and such at least one dry, inert nutrient into at least one sterile bioreactor chamber.

Storing 308 at least embodies herein the step of storing such at least one sterile bioreactor chamber containing such at least one dry, inert microbe and such at least one dry, inert nutrient.

Shipping 310 at least embodies herein the step of shipping such at least one sterile bioreactor chamber containing such at least one dry, inert microbe and such at least one dry, inert nutrient to at least one user.

Adding 312 water at least embodies herein the step of adding water to such at least one sterile bioreactor chamber containing such at least one dry, inert microbe and such at least one dry, inert nutrient.

Permitting 314 at least one bioreaction to occur at least embodies herein the step of permitting at least one bioreaction to occur.

Placing 316 at least embodies herein the step of placing such at least one dry, inert microbe into at least one water-soluble container prior to placing such at least one dry, inert microbe into such at least one sterile bioreactor chamber.

Placing 318 at least embodies herein the step of placing such at least one dry, inert nutrient into at least one water-soluble container prior to placing such at least one dry, inert nutrient into such at least one sterile bioreactor chamber.

Selecting 320 at least one dry, inert enzyme at least embodies herein the step of selecting at least one dry, inert enzyme adapted to support the life of such at least one dry, inert microbe.

Placing 322 such at least one dry, inert enzyme at least embodies herein the step of placing such at least one dry, inert enzyme into such at least one sterile bioreactor chamber.

Placing 324 at least embodies herein the step of placing such at least one dry, inert enzyme into at least one water-soluble container prior to placing such at least one dry, inert enzyme into such at least one sterile bioreactor chamber.

Selecting 332 at least embodies herein the step of selecting at least one dry, inert microbe.

Selecting 334 at least embodies herein the step of selecting at least one dry, inert nutrient adapted to support the life of such at least one dry, inert microbe.

Selecting 336 at least embodies herein the step of selecting at least one previously sterilized bioreactor chamber.

Receiving 338 at least embodies herein the step of receiving such at least one bioreactor chamber containing such at least one dry, inert microbe and such at least one dry, inert nutrient from at least one manufacturer.

Installing 340 at least embodies herein the step of installing such at least one bioreactor chamber containing such at least one dry, inert microbe and such at least one dry, inert nutrient in at least one bioreactor.

Adding fluid 342 at least embodies herein the step of adding fluid to such at least one bioreactor chamber containing such at least one dry, inert microbe and such at least one dry, inert nutrient.

Adding oxygen 344 at least embodies herein the step of adding oxygen to such at least one bioreactor chamber, after such step of adding fluid to such at least one bioreactor chamber.

Waiting 346 at least embodies herein the step of waiting for at least one bioreaction in such at least one bioreactor chamber to generate a useful number of live, active microbes.

Harvesting 348 at least embodies herein the step of harvesting such useful number of live, active microbes.

Adding 350 at least embodies herein the step of wherein the step of such step of harvesting such useful number of live, active microbe comprises the step of adding such useful number of live, active microbes into at least one irrigation system.

Uninstalling 352 at least embodies herein the step of uninstalling such at least one bioreactor chamber.

Disposing 354 at least embodies herein the step of disposing of such at least one bioreactor chamber.

Analyzing 362 at least embodies herein the step of analyzing at least one soil for at least one user.

Developing 364 at least embodies herein the step of developing at least one bioremediation prescription for such at least one analyzed soil.

Preloading 366 at least embodies herein the step of loading at least one bioreactor chamber with dry, inert microbes according to such at least one bioremediation prescription.

Providing 368 at least embodies herein the step of providing such at least one loaded bioreactor chamber to such at least one user.

Maintaining 370 at least embodies herein the step of maintaining at least one bioreactor on such at least one user's site.

Remotely monitoring 372 at least embodies herein the step of remotely monitoring such at least one bioreactor.

Installing 374 at least embodies herein the step of installing such at least one loaded bioreactor chamber in at least one bioreactor on such at least one user's site.

Installing 376 at least embodies herein the step of installing such at least one loaded bioreactor chamber in at least one bioreactor on such at least one user's site according to at least one maintenance schedule.

Applying 378 at least embodies herein the step of applying the bioreaction products of such at least one preloaded bioreactor chamber to such at least one analyzed soil.

Re-analyzing 380 at least embodies herein the step of re-analyzing such at least one analyzed soil to determine the effects of applying such bioreaction products.

Analyzing 392 at least embodies herein the step of analyzing at least one soil for at least one user.

Analyzing 394 at least embodies herein the step of analyzing at least one chemical treatment history of such at least one soil.

Developing 396 at least embodies herein the step of developing at least one bioremediation prescription for such at least one analyzed soil.

Providing 398 at least embodies herein the step of providing at least one on-site bioreactor wherein the step of such at least one on-site bioreactor comprises at least one programmable controller.

Providing 400 at least embodies herein the step of providing at least one loaded bioreactor chamber containing inert microbes, according to such at least one bioremediation prescription, adapted to be used with such on-site bioreactor.

Programming 402 at least embodies herein the step of programming such at least one on-site bioreactor to incubate such microbes in such at least one loaded bioreactor chamber.

Programming 404 at least embodies herein the step of programming such at least one on-site bioreactor to dispense such incubated microbes.

Developing 406 at least embodies herein the step of wherein the step of such step of developing at least one bioremediation prescription for such at least one analyzed soil is adapted to increase the functionality of crops grown in such at least one analyzed soil.

Developing 408 at least embodies herein the step of wherein the step of such step of developing at least one bioremediation prescription for such at least one analyzed soil is adapted to modify the growth of at least one cover crop grown in such at least one analyzed soil, wherein the step of the modification of the growth of such at least one cover crop has at least one beneficial effect on the growth of at least one cash crop grown in such at least one analyzed soil after such at least one cover crop.

Developing 410 at least embodies herein the step of wherein the step of such step of developing at least one bioremediation prescription for such at least one analyzed soil is adapted to benefit bodies of water adjacent such at least one analyzed soil.

Developing 412 at least embodies herein the step of wherein the step of such step of developing at least one bioremediation prescription for such at least one analyzed soil is adapted to decrease the concentration of toxins of crops grown in such at least one analyzed soil.

Although applicant has described applicant's preferred embodiments of this invention, it will be understood that the broadest scope of this invention includes modifications such as diverse shapes, sizes, and materials. Such scope is limited only by the below claims as read in connection with the above specification.

Further, many other advantages of applicant's invention will be apparent to those skilled in the art from the above descriptions and the below claims.

What is claimed is:

1. A bioreactor system, comprising:
    at least one flexible container containing therein a first soluble container containing therein at least one inert microbe, said at least one flexible container adapted to contain at least one fluid therein;
    at least one fluid input in fluid communication with said at least one flexible container and adapted to input fluid into said at least one flexible container to convert said at least one inert microbe into at least one live microbe, wherein said input fluid is adapted to convert said at least one inert nutrient into at least one available nutrient, convert at least one inert enzyme into at least one activated enzyme, and urge a bioreaction between said at least one live microbe, said at least one available nutrient, and said at least one activated enzyme;
    at least one fluid output in fluid communication with said at least one flexible container and adapted to receive output fluid from said at least one flexible container and dispense said output fluid;
    an enclosure enclosing said at least one flexible container and a temperature regulator that controls temperature in said enclosure, wherein said temperature regulator comprises at least one heat pump and at least one thermostat; and
    wherein each said flexible container held by a corresponding rigid stackable container such that each said at least one flexible container is not capable of motion with respect to said bioreactor system wherein said at least one flexible container comprises a plurality of said flexible containers and further comprising a controller adapted to sequentially control a time difference between a first time at which said at least one fluid input inputs fluid into said at least one flexible container and a second time at which said output fluid is received at said at least one fluid output, for each said flexible container, wherein said controller further comprises a computer programmed to receive input data from at least one sensor and to provide a bioremediation prescription in response to said input data, wherein said bioremediation prescription performed by said computer analyzes said input data, supplies fluid based on data analyzed with respect to said input data and supplies said fluid to a site in a prescribed manner based on said input data, said bioremediation prescription including a selection of said at least one inert microbe, and wherein said at least one sensor comprises at least one of a weather sensor, a soil moisture sensor, a soil temperature sensor, an air temperature sensor, a soil pH sensor, a soil nitrogen content sensor, a soil oxygen content sensor and a soil intensity sensor.

2. The bioreactor system as in claim 1, wherein said first soluble container comprises a water soluble container formed of polyvinyl alcohol plastic.

3. The bioreactor system as in claim 1, further comprising said at least one flexible container further containing therein a second soluble container containing therein at least one substantially dry inert nutrient and a third soluble container containing therein at least one substantially dry inert enzyme.

4. The bioreactor system as in claim 1, wherein said at least one flexible container comprises a plurality of said flexible containers and said corresponding plurality of rigid stackable containers are stacked over one another.

5. The bioreactor system as in claim 1, wherein said at least one inert microbe comprises a microbe in a substantially wet state.

6. The bioreactor system as in claim 1, wherein said at least one inert microbe comprises a microbe in a substantially dry state.

7. The bioreactor system as in claim 6, further comprising:
at least one gas input that provides fluid communication with said at least one flexible container and is adapted to input at least one gas into said at least one flexible container and create bubbles in said at least one fluid;
at least one gas output that provides fluid communication with said at least one flexible container and is adapted to output said at least one gas from said at least one flexible container.

8. The bioreactor system as in claim 1, further comprising at least one gas input that inputs at least one gas into said at least one flexible container and at least one gas output that outputs said at least one gas from said at least one flexible container, wherein said at least one gas input creates bubbles in said at least one fluid.

9. A method for causing bioreaction comprising:
providing at least one flexible container containing therein a first soluble container containing therein at least one inert microbe wherein said at least one flexible container comprises a plurality of said flexible containers and further comprising a controller programmed to sequentially control a time difference between a first time at which said at least one fluid input inputs fluid into said at least one flexible container and a second time at which said output fluid is received at said at least one fluid output, for each said flexible container, wherein said controller further comprises a computer adapted to receive input data from at least one sensor and to provide a bioremediation prescription in response to said input data, wherein said bioremediation prescription performed by said computer analyzes said input data, supplies fluid based on data analyzed with respect to said input data and supplies said fluid to a site in a prescribed manner based on said input data, said bioremediation prescription including a selection of said at least one inert microbe, and wherein said at least one sensor comprises at least one of a weather sensor, a soil moisture sensor, a soil temperature sensor, an air temperature sensor, a soil pH sensor, a soil nitrogen content sensor, a soil oxygen content sensor and a soil intensity sensor;
enclosing said at least one flexible container and a temperature regulator that controls temperature in an enclosure, wherein said temperature regulator comprises at least one heat pump and at least one thermostat;
delivering input fluid via at least one fluid input into said at least one flexible container thereby dissolving said first soluble container and urging said at least one inert microbe to be converted into at least one live microbe, wherein said input fluid is adapted to convert said at least one inert nutrient into at least one available nutrient, convert at least one inert enzyme into at least one activated enzyme, and urge a bioreaction between said at least one live microbe, said at least one available nutrient, and said at least one activated enzyme;
harvesting by dispensing an output fluid comprising at least said at least one live microbe via at least one fluid output.

10. The method as in claim 9, wherein said inert microbe comprises a substantially dry inert microbe.

11. The method as in claim 9, wherein said first soluble container is a first water soluble container.

12. The method as in claim 9, further comprising:
providing at least one substantially dry inert nutrient and at least one substantially dry inert enzyme within said at least one flexible container; and
wherein said output fluid includes products of said bioreaction.

13. The method as in claim 12, wherein:
said first soluble container is a first water soluble container;
said providing at least one substantially dry inert nutrient and at least one substantially dry inert enzyme comprises said at least one flexible container including therein a second water soluble container containing therein said at least one substantially dry inert nutrient and a third water soluble container containing therein said at least one substantially dry inert enzyme; and
said delivering further comprises dissolving said second water soluble container and said third, water soluble container.

14. The method as in claim 9, further comprising delivering input gas via a gas input port, to said at least one flexible container, and delivering output gas via a gas output port, from said at least one flexible container.

15. The method as in claim 10, further comprising:
providing at least one substantially dry inert nutrient and at least one substantially dry inert enzyme within said at least one flexible container; and
wherein said output fluid includes products of said bioreaction.

16. The method as in claim 11, further comprising:
providing at least one substantially dry inert nutrient and at least one substantially dry inert enzyme within said at least one flexible container; and
wherein said output fluid includes products of said bioreaction.

17. The method as in claim 15, further comprising delivering input gas via a gas input port, to said at least one flexible container, and delivering output gas via a gas output port, from said at least one flexible container.

18. The method as in claim 16, further comprising delivering input gas via a gas input port, to said at least one flexible container, and delivering output gas via a gas output port, from said at least one flexible container.

* * * * *